United States Patent
Bosanac et al.

(10) Patent No.: US 12,201,415 B2
(45) Date of Patent: Jan. 21, 2025

(54) ANALYSING A BODY

(71) Applicant: Body Composition Technologies Pty Ltd, Perth (AU)

(72) Inventors: Vlado Bosanac, Subiaco (AU); Martin Howard Otway, Singapore (SG); Amar El-Sallam, Subiaco (AU)

(73) Assignee: Body Composition Technologies Pty Ltd, Perth (AU)

( * ) Notice: Subject to any disclaimer, the term of this patent is extended or adjusted under 35 U.S.C. 154(b) by 530 days.

(21) Appl. No.: 17/417,163

(22) PCT Filed: Dec. 19, 2019

(86) PCT No.: PCT/AU2019/051416
§ 371 (c)(1),
(2) Date: Jun. 22, 2021

(87) PCT Pub. No.: WO2020/132713
PCT Pub. Date: Jul. 2, 2020

(65) Prior Publication Data
US 2022/0087533 A1    Mar. 24, 2022

(30) Foreign Application Priority Data
Dec. 24, 2018 (AU) ................................ 2018904941

(51) Int. Cl.
*A61B 5/00* (2006.01)
*A61B 5/107* (2006.01)
(Continued)

(52) U.S. Cl.
CPC .......... *A61B 5/1079* (2013.01); *A61B 5/0013* (2013.01); *A61B 5/0064* (2013.01);
(Continued)

(58) Field of Classification Search
CPC . A61B 2576/02; A61B 5/0013; A61B 5/0022; A61B 5/0064; A61B 5/0073;
(Continued)

(56) References Cited

U.S. PATENT DOCUMENTS 8,588,495 B2  11/2013  Gupta et al.
9,740,710 B2   8/2017  Han et al.
(Continued)

FOREIGN PATENT DOCUMENTS

CN    104799828 A    7/2015
CN    105359161 A    2/2016
(Continued)

OTHER PUBLICATIONS

Office Action in CN 201980092875.X dated Aug. 30, 2023, 22 pages.
(Continued)

*Primary Examiner* — Michael T Rozanski
(74) *Attorney, Agent, or Firm* — MARSHALL, GERSTEIN & BORUN LLP

(57) ABSTRACT

In one aspect, a system 10 for analysing a body 14 using a device 12 is disclosed. In one arrangement and embodiment, the device 12 comprises: a controller 18; storage 20 storing electronic program instructions for controlling the controller 18; and an input means. In one form, the controller is operable, under control of the electronic program instructions, to: receive input via that input means, the input comprising at least one representation of the body 14; process the input to conduct an analysis of the body 14 and generate an output on the basis of the analysis, the processing comprising using a database 40; and communicate the output via a display 22. In an embodiment, the output comprises an estimation of an individuals three-dimensional (3D) body shape and associated body measurements, com-
(Continued)

position and health and wellness risks from a representation comprising human imagery.

25 Claims, 19 Drawing Sheets

(51) Int. Cl.
| | | |
|---|---|---|
| *G06N 20/00* | (2019.01) | |
| *G06T 19/00* | (2011.01) | |
| *G06V 40/10* | (2022.01) | |
| *G16H 50/20* | (2018.01) | |
| *G16H 50/30* | (2018.01) | |

(52) U.S. Cl.
CPC .......... *A61B 5/0073* (2013.01); *A61B 5/7435* (2013.01); *A61B 5/744* (2013.01); *A61B 5/7485* (2013.01); *G06N 20/00* (2019.01); *G06T 19/00* (2013.01); *G06V 40/103* (2022.01); *G16H 50/20* (2018.01); *G16H 50/30* (2018.01); *A61B 2576/02* (2013.01); *G06T 2207/30004* (2013.01); *G06T 2210/41* (2013.01)

(58) Field of Classification Search
CPC ..... A61B 5/055; A61B 5/1079; A61B 5/4872; A61B 5/7267; A61B 5/7275; A61B 5/7435; A61B 5/744; A61B 5/7485; G06M 20/00; G06T 19/00; G06T 2207/30004; G06T 2210/41; G06V 40/103; G16H 30/40; G16H 50/20; G16H 50/30
See application file for complete search history.

(56) References Cited

U.S. PATENT DOCUMENTS

| | | | |
|---|---|---|---|
| 9,792,681 | B2 | 10/2017 | Bryan et al. |
| 9,839,376 | B1 | 12/2017 | Ross et al. |
| 9,949,697 | B2 | 4/2018 | Iscoe et al. |
| 11,331,039 | B2 | 5/2022 | Matsumoto et al. |
| 2009/0099457 | A1 | 4/2009 | Barnes |
| 2013/0325493 | A1 | 12/2013 | Wong et al. |
| 2013/0336550 | A1 | 12/2013 | Kapur et al. |
| 2016/0253798 | A1 | 9/2016 | Barrett et al. |
| 2017/0164832 | A1 | 6/2017 | Kaib et al. |
| 2018/0289334 | A1 | 10/2018 | De Brouwer et al. |

FOREIGN PATENT DOCUMENTS

| | | |
|---|---|---|
| CN | 106999107 A | 8/2017 |
| CN | 107077736 A | 8/2017 |
| CN | 108198620 A | 6/2018 |
| EP | 1993443 B1 | 11/2015 |
| JP | 2018-504663 A | 2/2018 |
| WO | WO-2007/096652 A2 | 8/2007 |
| WO | WO-2015/050929 A1 | 4/2015 |
| WO | WO-2016/072926 A1 | 5/2016 |
| WO | WO-2016/086266 A1 | 6/2016 |
| WO | WO-2017/141958 A1 | 8/2017 |

OTHER PUBLICATIONS

Search Report and Written Opinion in International Application No. PCT/AU2019/051416 dated Jan. 20, 2020, 9 pages.
Extended European Search Report in EP Application No. 19903106.3 dated Aug. 4, 2022, 7 pages.
Notice of Reasons for Rejection in JP Application No. 2021-556646 dated Aug. 8, 2023, 12 pages.
Corrected Written Opinion in SG Application No. 11202106762U dated Mar. 20, 2023, 7 pages.
Invitation to Respond to Written Opinion in SG Application No. 11202106762U dated Mar. 21, 2023, 2 pages.
Examination Report in Indian Patent Application No. 202137032459 dated Feb. 24, 2023, 10 pages.
Invitation to Respond to Written Opinion and Written Opinion in Singaporean Patent Application No. 11202106762U dated Feb. 12, 2023, 9 pages.
Examination Report in EP Application No. 2019412503 dated Jul. 2, 2024, 3 pages.
Examination Report in CA Application No. 3,124,572 dated Mar. 15, 2024, 4 pages.
Second Office Action in CN Application No. 201980092875.X dated Apr. 25, 2024, 24 pages.
Notice to Grant a Patent in CN Application No. 201980092875.X dated Sep. 25, 2024, 5 pages.

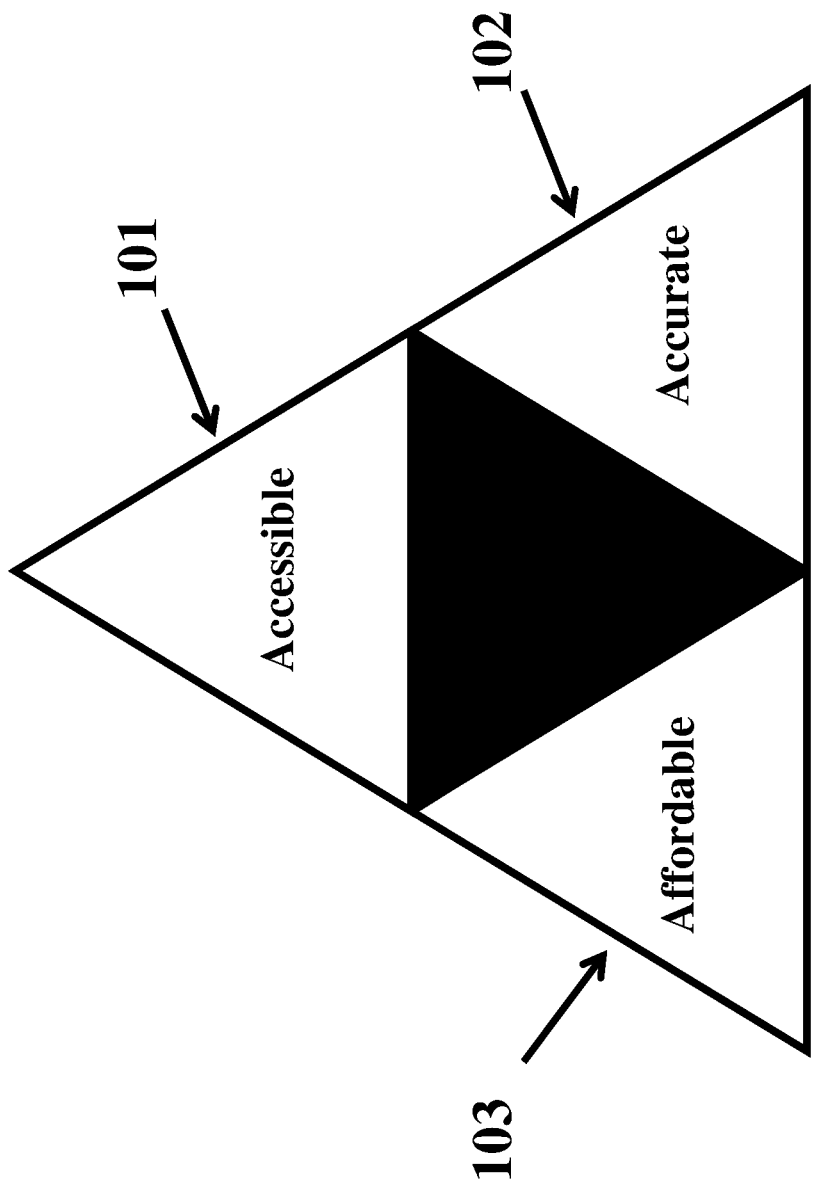
Figure 1: Theoretically ideal body composition measurement model

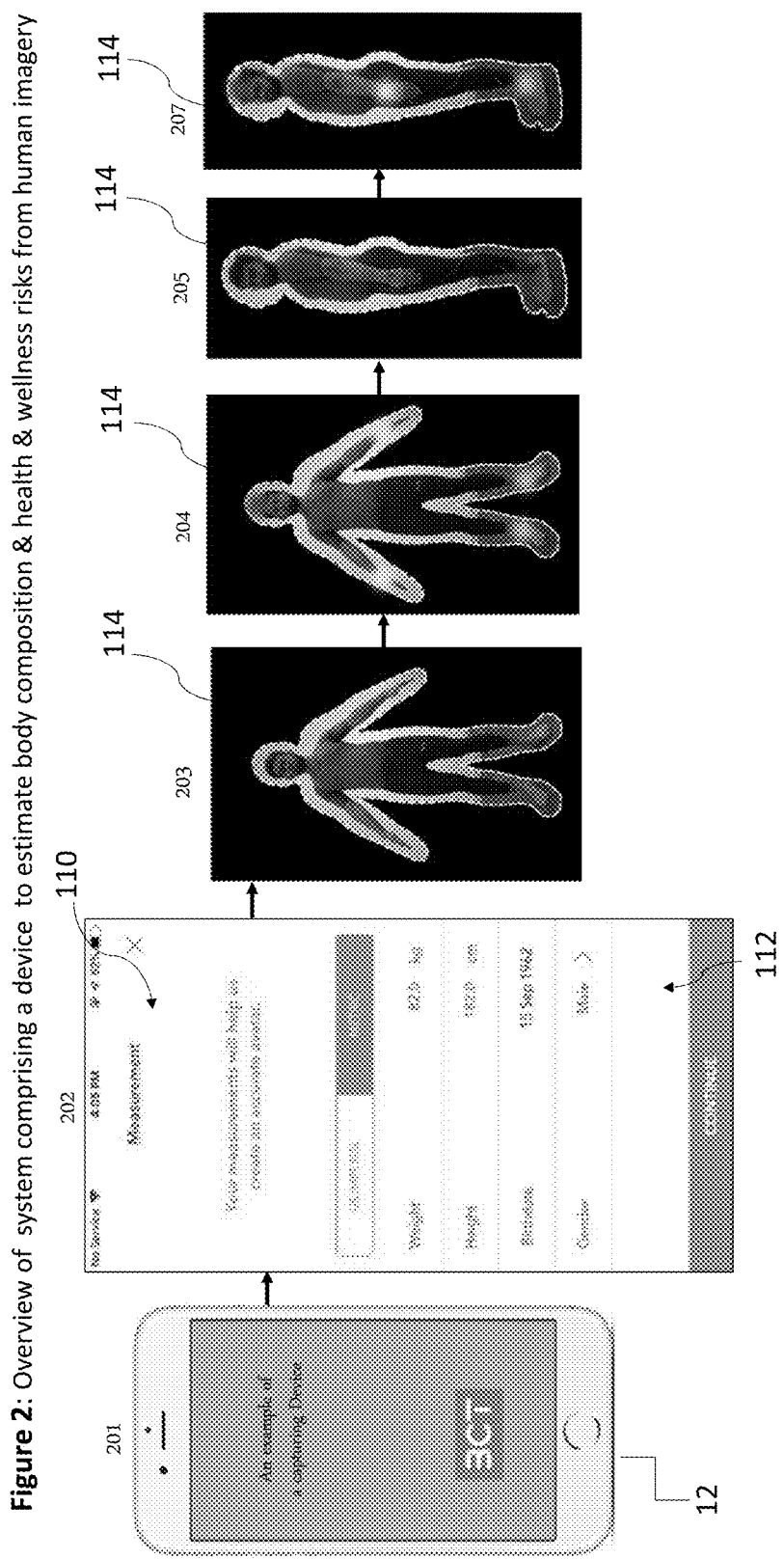
Figure 2: Overview of system comprising a device to estimate body composition & health & wellness risks from human imagery

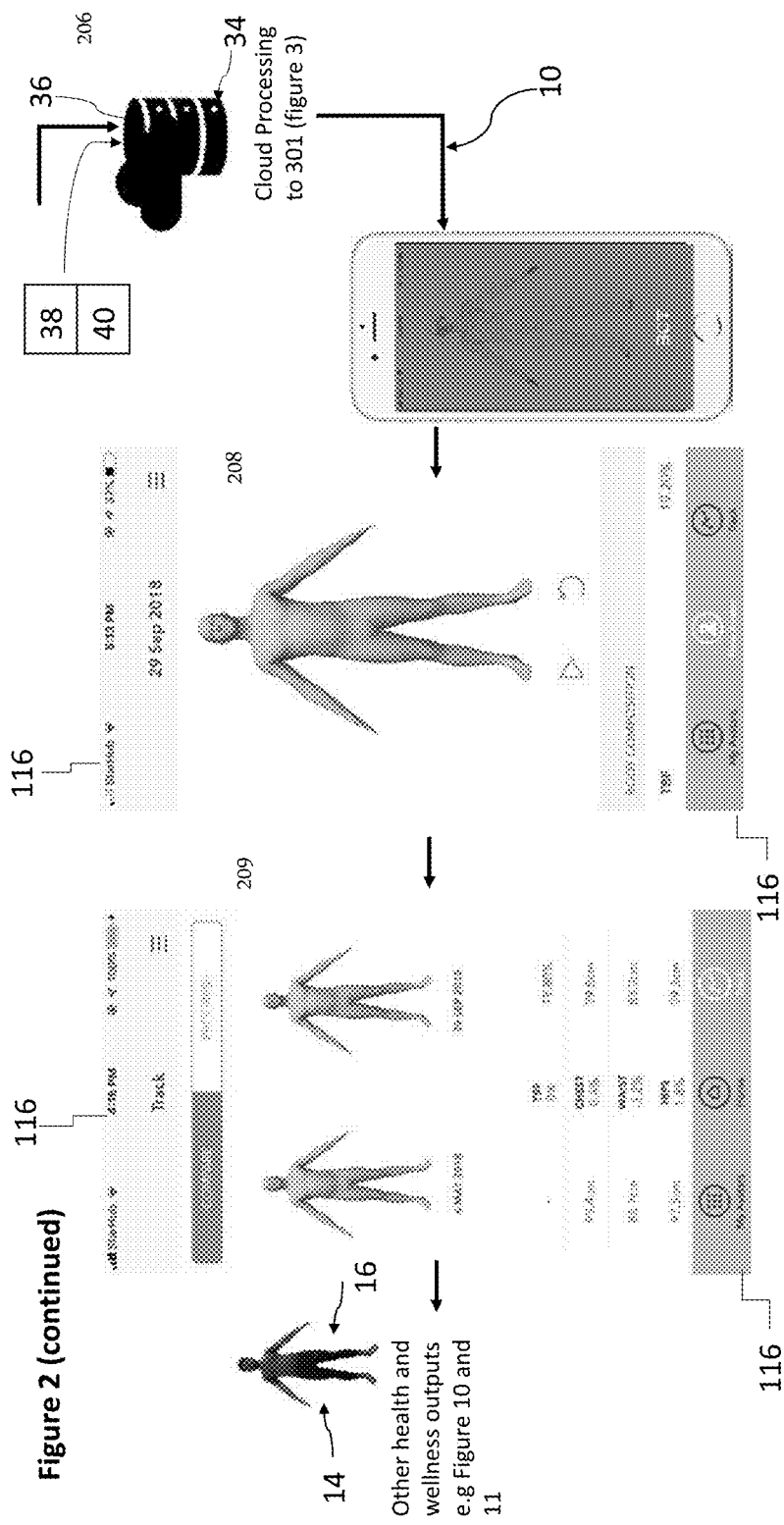

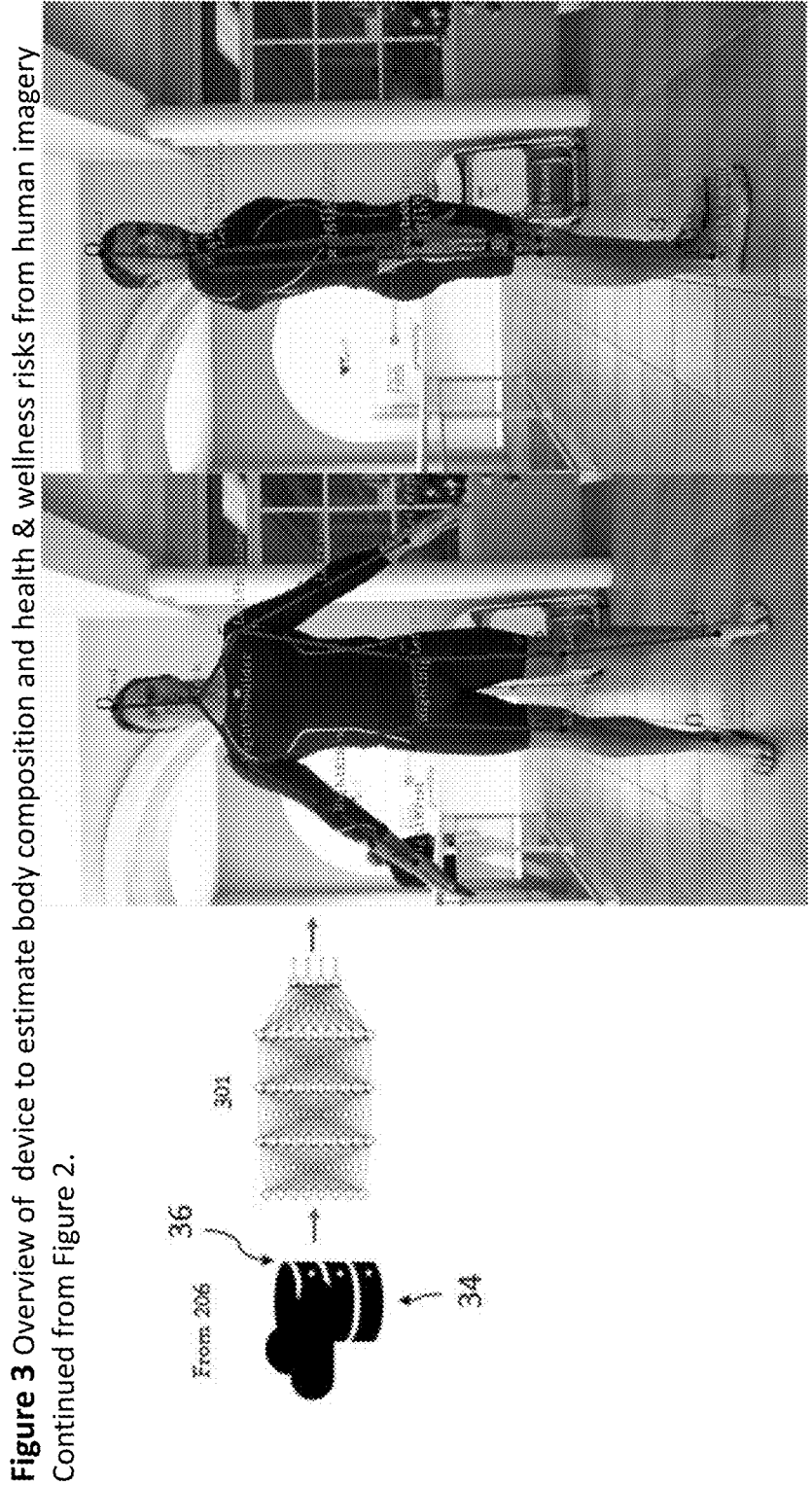
Figure 3 Overview of device to estimate body composition and health & wellness risks from human imagery Continued from Figure 2.

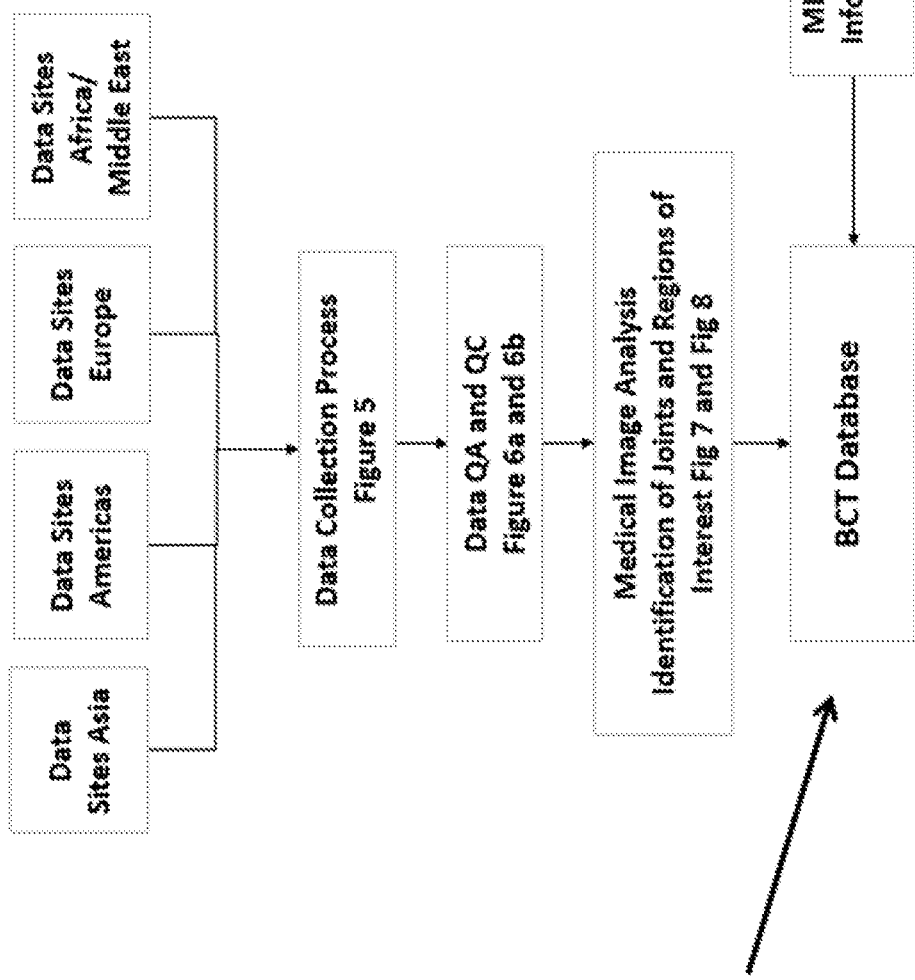

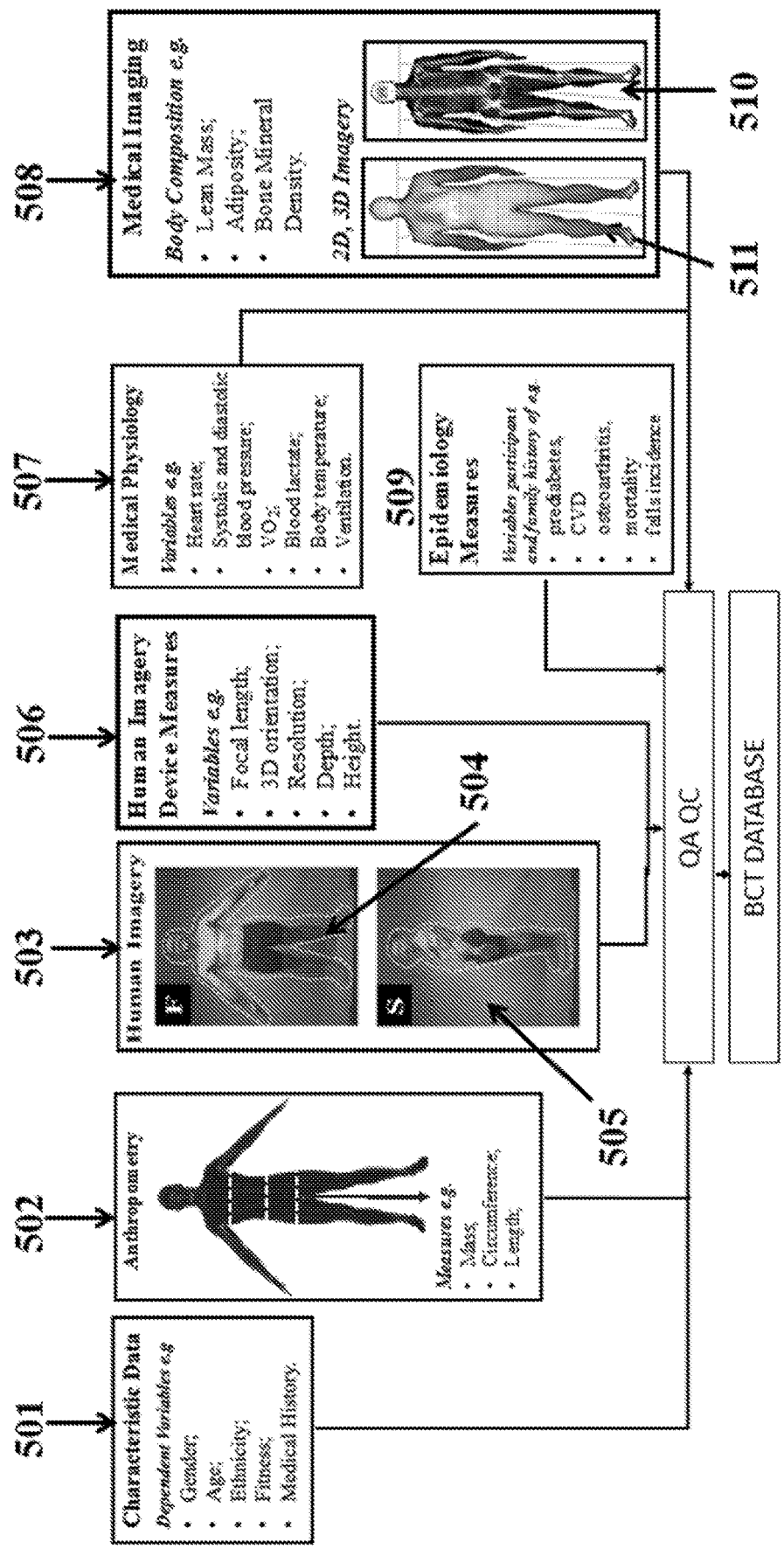

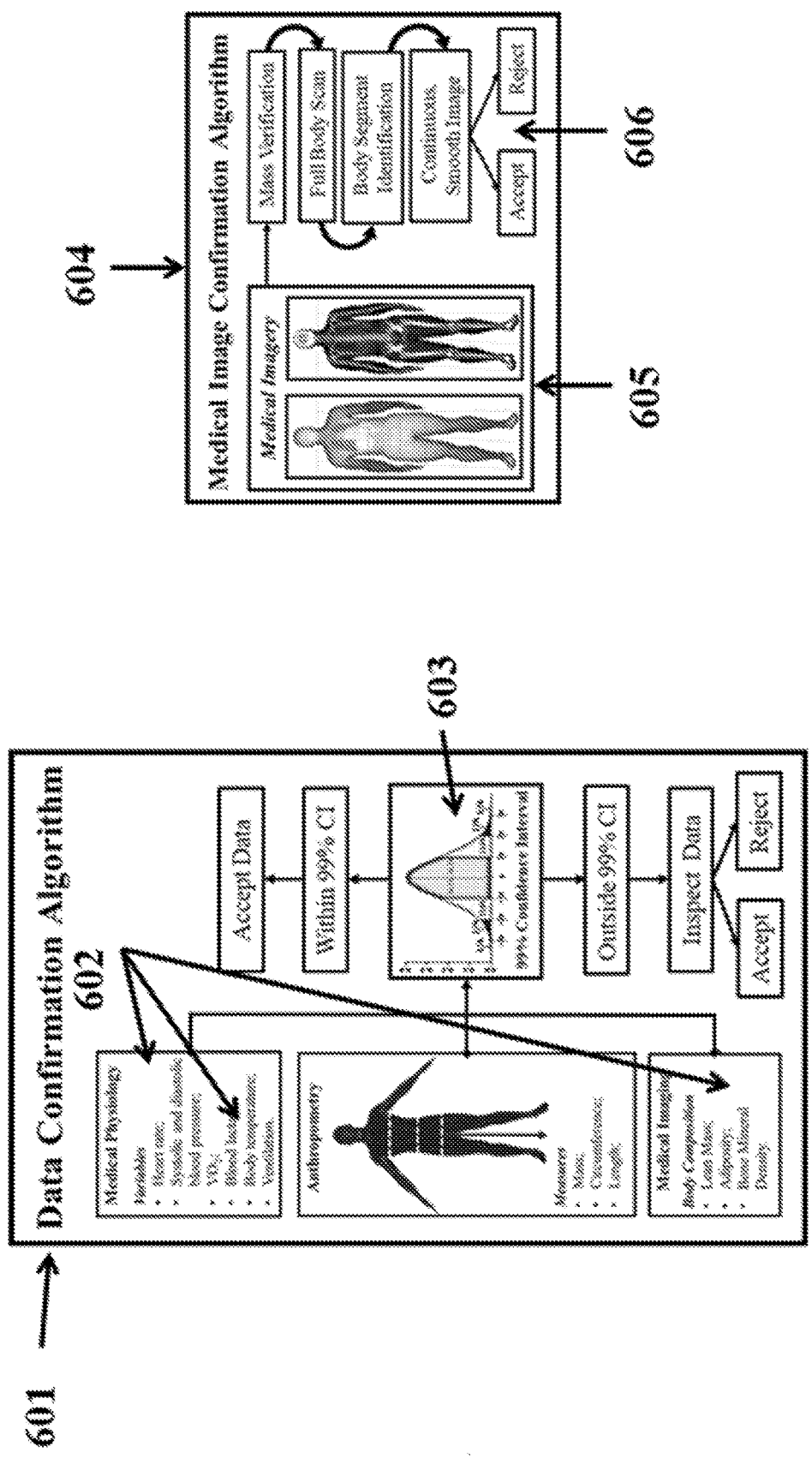
Figure 6a General overview of data, medical imagery and human imagery quality control procedures

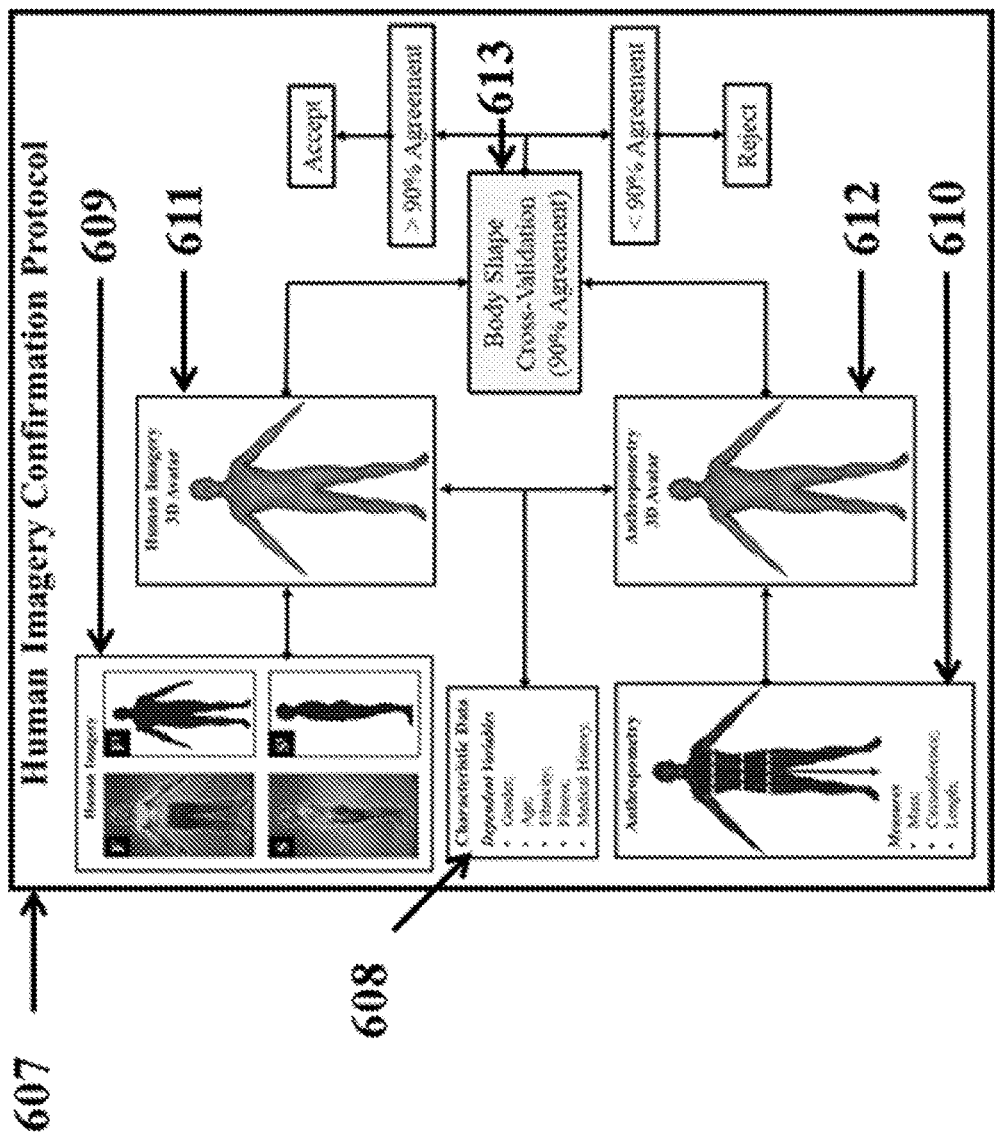
Figure 6b: General overview of data, medical imagery and human imagery quality control procedures

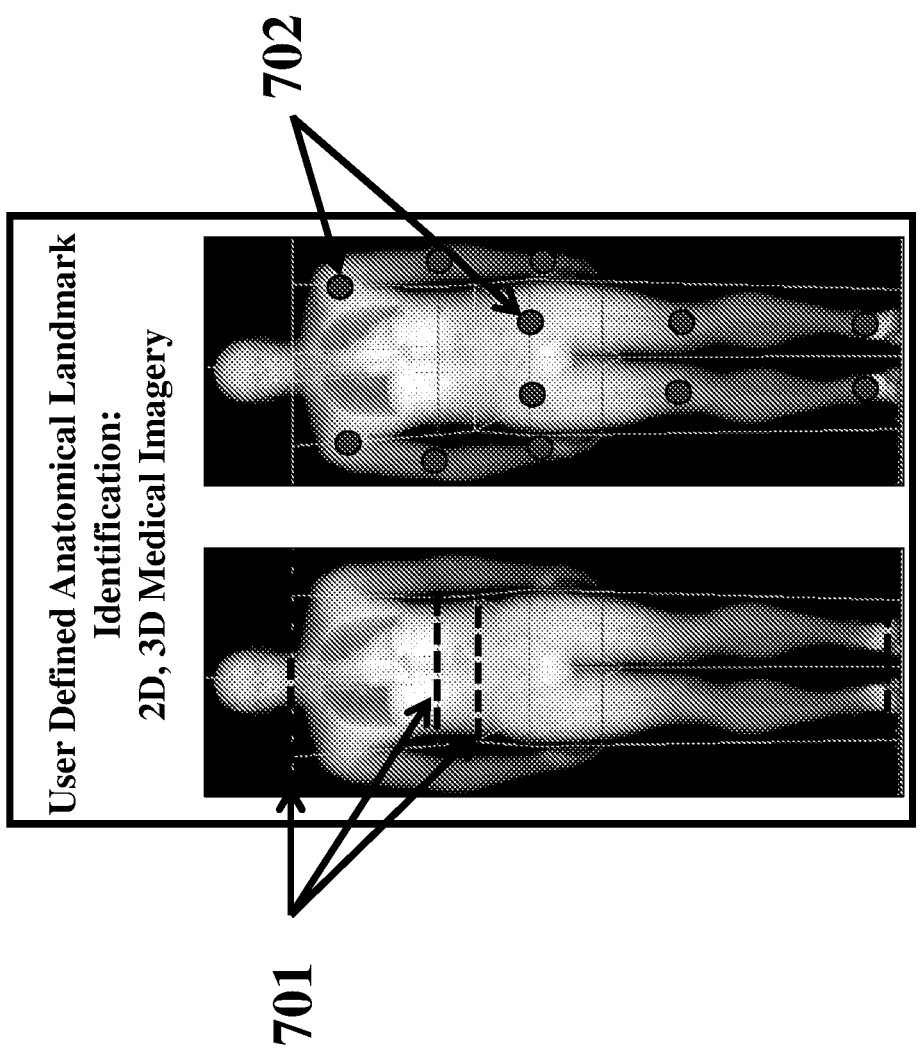
Figure 7: General overview of user defined anatomical landmark identification process.

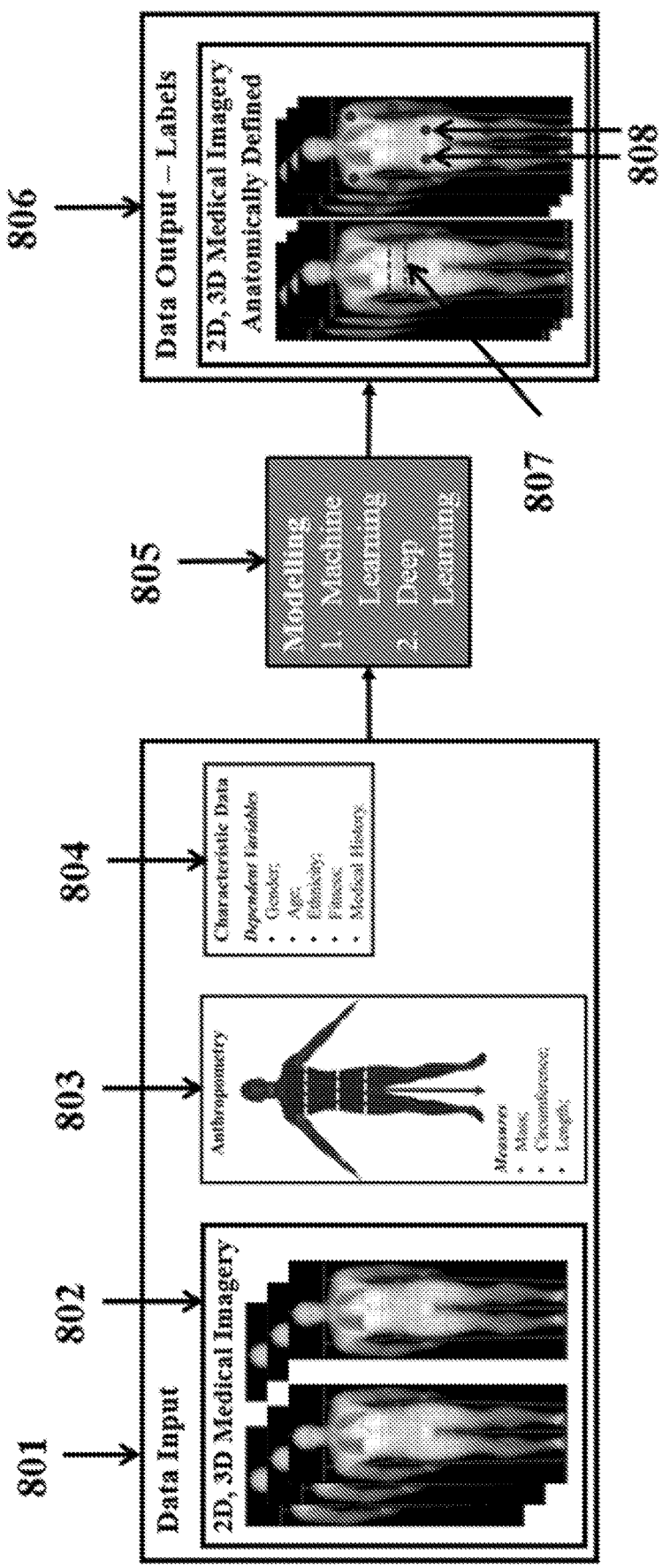
Figure 8: General overview of automated deep neural network for defining anatomical landmarks within medical images. Joint centres are identified with red dots, region lines with red dotted lines.

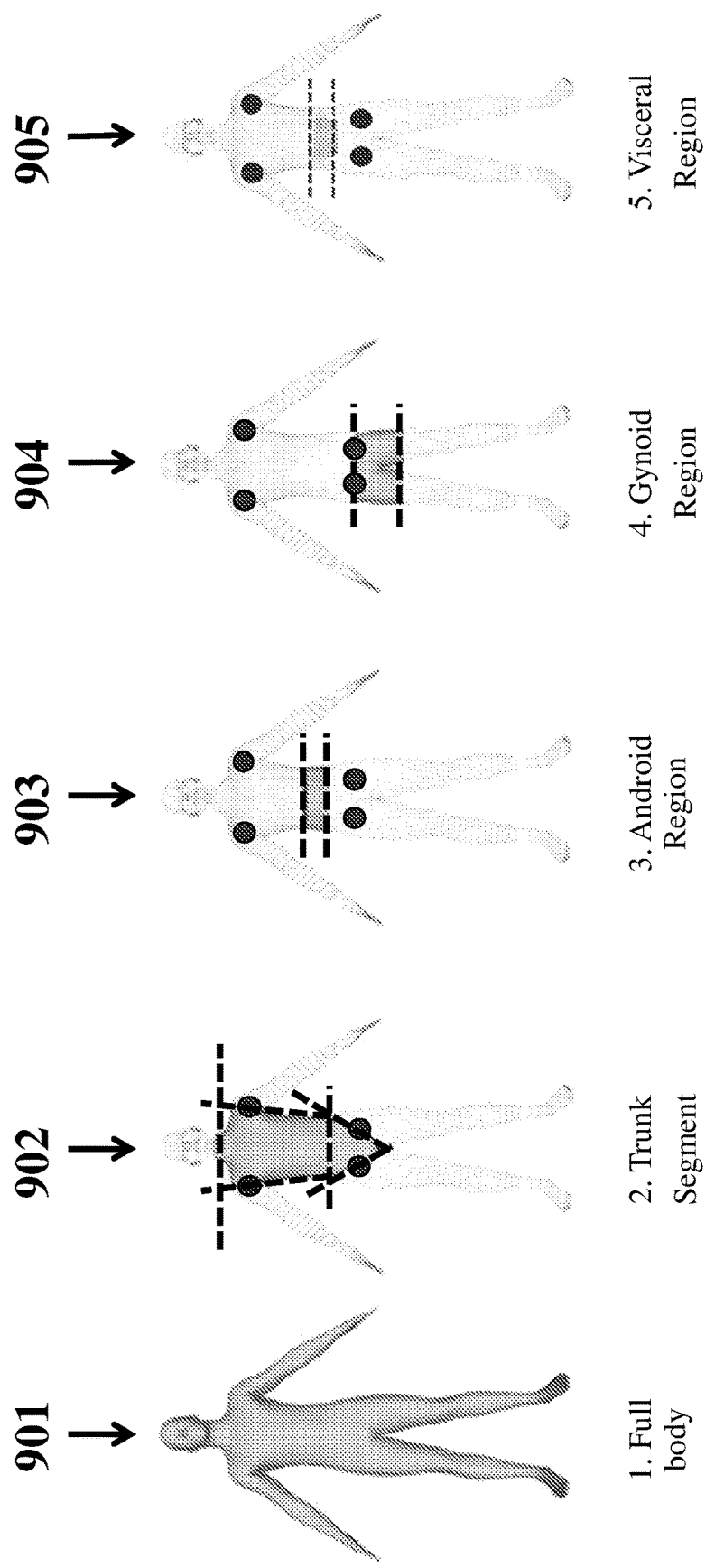
Figure 9: General overview of anatomical landmarks registered within participant specific 3D shape. Joint centre positions assist the AI/ML model in the definition of region lines.

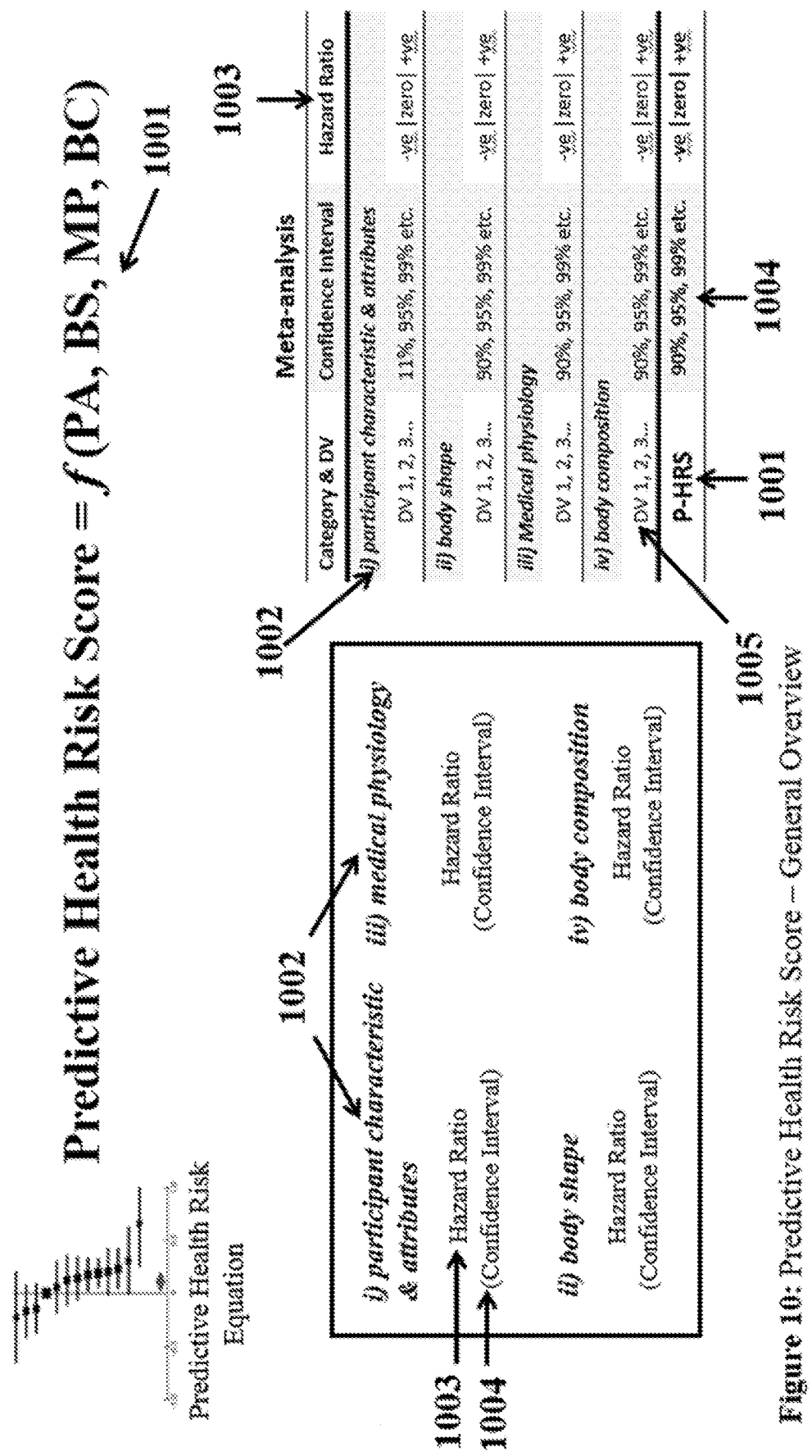
Figure 10: Predictive Health Risk Score — General Overview

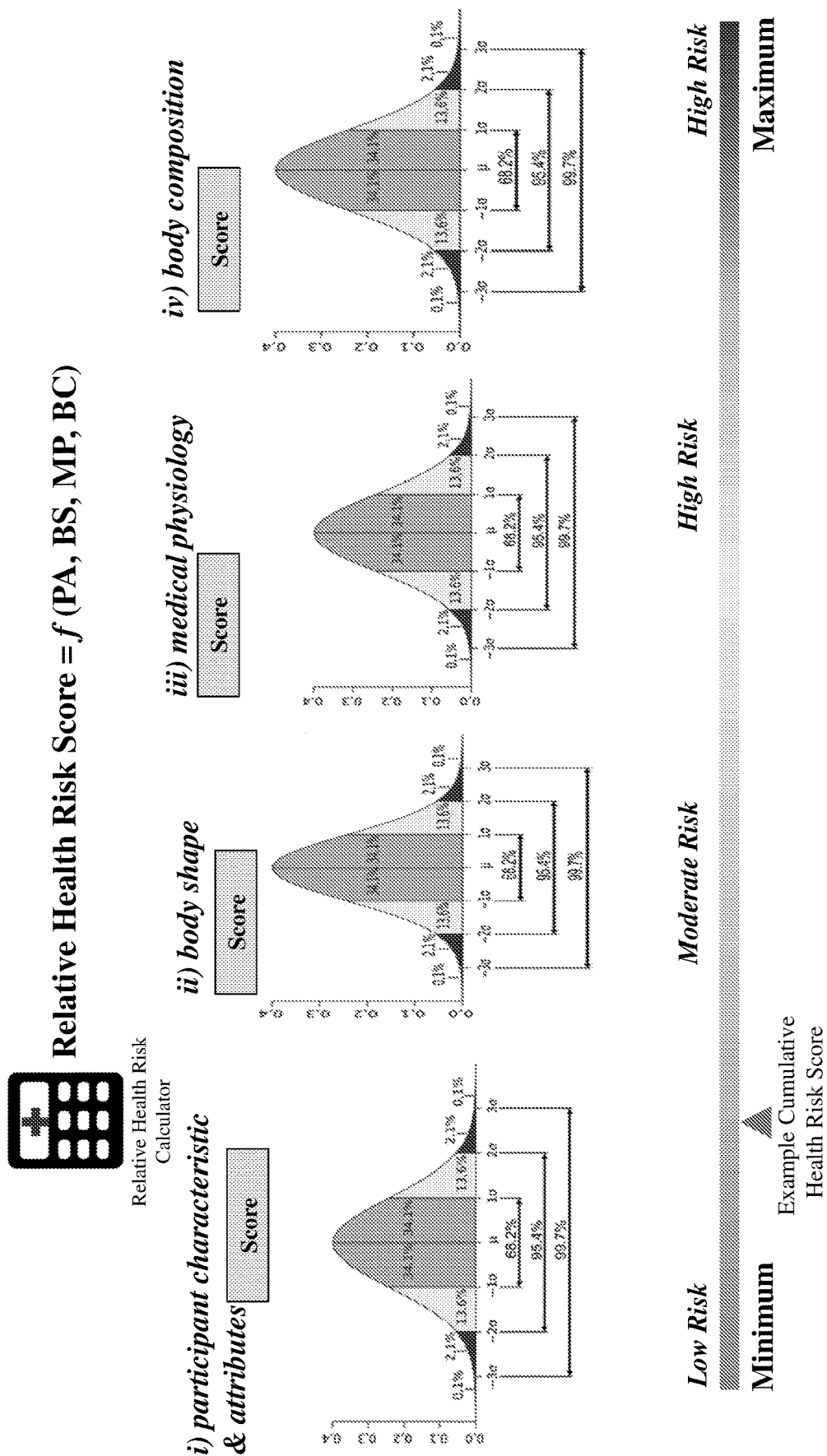
Figure 11: Relative Health Risk Calculator – General Overview

An example of body part segmentation without the use of joints estimated based on medical imaging Example Body Part Segmentation using estimated anatomical landmarks and joints.

ANALYSING A BODY

CROSS-REFERENCE TO RELATED APPLICATIONS

This application is the U.S. national phase of International Patent Application No. PCT/AU2019/051416 filed Dec. 19, 2019, which claims the priority benefit of Australia Application No. 2018904941 filed on Dec. 24, 2018, the entire respective disclosures of which are incorporated herein by reference.

FIELD OF THE INVENTION

The present invention relates generally to analysing a body.

The present invention will be described with particular reference to analysing a human body to provide an estimation of an individual's three-dimensional (3D) body shape and its associated body composition and health and wellness risks. However, it will be appreciated that the invention is not limited to this particular field of use, it may be used in respect of bodies of other things, and for performing an analysis for additional and/or alternative purposes.

BACKGROUND

Any discussion of the background art throughout the specification should in no way be considered as an admission that such background art is prior art, nor that such background art is widely known or forms part of the common general knowledge in the field in Australia or worldwide.

All references, including any patents or patent applications, cited in this specification are hereby incorporated by reference. No admission is made that any reference constitutes prior art. The discussion of the references states what their authors assert, and the applicant reserves the right to challenge the accuracy and pertinence of the cited documents. It will be clearly understood that, although a number of prior art publications are referred to herein, this reference does not constitute an admission that any of these documents forms part of the common general knowledge in the art, in Australia or in any other country.

The management, treatment and monitoring of prediabetes, chronic health, premature mortality, and musculoskeletal disorders are growing global health care concerns, costing governments worldwide trillions of dollars annually. From a recent study published by the World Economic Forum (Kate Kelland. Chronic disease to cost $47 trillion by 2030: WEF. Published on-line, 19 Sep. 2011), it was estimated that the management of chronic health diseases alone will reach over 46 trillion dollars within 20 years.

It has been established that non-communicable diseases (i.e., chronic diseases) like cardiovascular disease and type II diabetes are growing global healthcare concerns (GBD 2016 Causes of Death Collaborators. Global, regional, and national age-sex specific mortality for 264 causes of death, 1980-2016: a systematic analysis for the Global Burden of Disease Study 2016. *The Lancet.* 390(10100):1151-1210; and WHO. Global action plan for the prevention and control of noncommunicable diseases 2013-2020. Geneva, Switzerland: World Health Organization, 2013. Keys, A., Karvonen, N., Kimura, N., Taylor, H. L.). Adiposity, which is a measurement characteristic of obesity, has been identified by the World Health Organization (WHO) as a primary target towards reducing chronic disease and related deaths worldwide. With the disclosure that obesity, which can be directly or indirectly assessed through the measurement of an individual's body shape/composition, is linked to the development of chronic diseases, it is important for researchers, underwriters, and health care professionals, amongst others, to understand which measures are reliable, as well as relevant for estimating chronic disease risk. This is important, so that more reliable, sensitive and specific risk estimates can be developed, which may translate to 1) reductions in global health care costs through population monitoring and early tailored intervention(s) and 2) reduction in claims paid by insurers and reinsurers corresponding to improvements in underwriting standards.

Since 1980, cardiovascular disease and the incidence of diabetes have increased around the world (Anand, S. and Yusuf, S. (2011). Stemming the global tsunami of cardiovascular disease. *The Lancet.* 377(9765):529-532; NCD Risk Factor Collaboration (2016). Worldwide trends in diabetes since 1980: a pooled analysis of 751 population-based studies with 4.4 million participants. *The Lancet.* 387(10027):1513-1530.). In this relatively short time period in human history, world diabetes rates have increased from 108 million to a staggering 422 million people. The number of people classified as prediabetic has also dramatically increased, with more than 470 million people worldwide expected to be diagnosed as prediabetic by 2030 (Tabák, A. G., Herder, C., Rathmann, W Brunner, E J., Kivimäki, M. (2012). Prediabetes: A high-risk state for developing diabetes. 379(9833): 2279-2290.). Recent statistics are also showing knee and hip joint osteoarthritis are having significant and increased impacts on world health care costs as our global population ages (Allen, K. and Golightly, Y., 2015 Epidemiology of osteoarthritis: state of the evidence). With larger numbers of older adults among our current world population, the healthcare costs associated with falls risk and sarcopenia, which is the excessive lean muscle mass loss through the human aging process, have been growing rapidly. In the United States (US), the prevalence of sarcopenia was estimated to be between 14% to 33% among older adult populations within long-term care facilities. The associated health care costs of sarcopenia in the US have been estimated to be $42.1 billion dollars annually in 2000 (Cruz-Jentoft A J, Landi F, Schneider S M, et al. Prevalence of and interventions for sarcopenia in aging adults: a systematic review. Report of the International Sarcopenia Initiative (EWGSOP and IWGS). *Age Aging.* 2014; 43:748-759).

A contributing, but modifiable, risk factor to prediabetes, chronic health, mortality (GBD, 2016), musculoskeletal disorders, sarcopenia and falls risk is an individual's body composition (i.e., lean muscle mass, total adiposity and central adiposity).

In response to these alarming world trends, healthcare systems and government agencies worldwide have invested, and continue to invest, much time and money in the monitoring of their population's body composition, with special interest in their body composition (i.e., lean mass, adiposity and bone mineral density). It is also important for government and allied health professionals to understand which measures are relevant for predicting prediabetes, chronic disease, mortality and musculoskeletal disorders. This is important, so that reliable, sensitive and specific relative and predictive health risk techniques and equations can be developed.

Key body composition measurements for predicting chronic disease and mortality are those centred around the measurement of central or abdominal adiposity (WHO; Pischon et al. (2008). General and Abdominal Adiposity and Risk of Death in Europe. N Engl J Med 2008; 359:2105-2120. DOI: 10.1056/NEJMoa0801891; Jacobs et al. (2010). Waist Circumference and All-Cause Mortality in a Large US Cohort. Arch Intern Med. 2010 Aug. 9; 170(15):1293-301.). Central adiposity measures include android fat, gynoid fat, visceral fat, waist circumference and waist to hip ratio. Of the many central adiposity measures available, visceral adiposity has surfaced as a critical body composition variable for prediction of an individual's risk of developing chronic health disorders like heart disease and diabetes (Ding Y., Gu D., Zhang Y., Han W., Liu H., Qu Q. (2015). Significantly increased visceral adiposity index in prehypertension. PLoS One. 10;10(4):e0123414; Hanley A J, Wagenknecht L E, Norris J M, Bryer-Ash M, Chen Y I, Anderson A M, Bergman R, Haffner S M. Insulin resistance, beta cell dysfunction and visceral adiposity as predictors of incident diabetes: the Insulin Resistance Atherosclerosis Study (IRAS) Family study. Diabetologia 52: 2079-2086, 2009; Ghroubi, S., Elleuch, H., Guermazi, M., Kaffel, N., Feki, H.; Abid, M., Baklouti, S.; Elleuch, M. H. (2007). "Abdominal obesity and knee ostheoarthritis". Annales de Réadaptation et de Médecine Physique. 50 (8): 661-666. doi:10.1016/j.annrmp.2007.03.005.).

There is much research showing that an individual's total and central adiposity measures are elevated among prediabetic and diabetic populations when compared to normal, healthy populations. With a relationship between an individual's body composition and prediabetes and diabetes, there is opportunity to develop relative risk or predictive equations to estimate an individual's prediabetes and diabetes risk from their body composition and relevant participant characteristic, anthropometry and epidemiology (i.e., prediabetes and diabetes status) information. With the current, conventional method to screen or diagnose prediabetes or diabetes being an invasive, painful and time and cost expensive blood test (i.e., fasting plasma glucose, HbA1c), there is a need for a low cost, non-invasive and accurate method within the market.

For the effective monitoring and screening of sarcopenia as an example, lean body composition measures would be of interest, and specifically, lean muscle mass and appendicular lean muscle mass (Matthew J. Delmonico, PhD, MPH, and Darren T. Beck, PhD. (2017).The Current Understanding of Sarcopenia: Emerging Tools and Interventional Possibilities. American Journal of Lifestyle Medicine.). Lean muscle mass, and particularly that of the lower limb, would also be important for the screening and monitoring of falls risk among older adults. With it being disclosed that one-year mortality rates increase to 90% among populations >70 years who suffer a fall related hip or pelvis fracture, it is important that we possess cost effective and accurate methods for the screening and monitoring of this population.

The reason that body composition measures like lean muscle mass and adiposity are of particular interest for the management of prediabetes, chronic health conditions, mortality and musculoskeletal disorders is because they are modifiable factors. If an individual is able to measure relevant body composition variables easily and affordably then they can focus on modifying those body composition variables that can improve their health and wellness risk. This can then lead to reductions in prediabetes diagnoses, chronic disease, premature mortality, musculoskeletal disease and falls related risks, improving health outcomes and reducing health related expenditures. However, to do this effectively requires a body composition measurement tool approaching a theoretical ideal.

For a general population, an ideal body composition measurement tool, in theory, must firstly be able to measure the correct variables—meaning the variables that are related to an individual's general health and overall well-being.

Secondly, the measurement of body composition variables must be affordable, accessible and accurate.

An illustration of an ideal body composition measurement model is depicted in FIG. 1 of the drawings. This should be used in the context of the prior art to better understand the current state of the prior art currently in the market space and to also understand how embodiments of the present invention seek to close the current market gap.

Without an efficient, affordable and easy to use tool that can estimate body composition measurement, government agencies and health care providers are left with incomplete health information for the effective monitoring and/or treatment of chronic health and musculoskeletal disorders over their population's lifespan, as well as an individual's risk of premature mortality. This places significant barriers on a health care system's ability to prevent, manage and treat chronic health and musculoskeletal disorders like heart disease, prediabetes, diabetes, joint osteoarthritis and sarcopenia as well as to predict premature mortality.

Established criterion measures for the reliable, in-vivo measurement of body composition variables like central and whole-body adiposity and lean muscle mass are medical imaging technologies (Duren, D., Sherwood, R., Czerwinski, S. et al. (2008). Body Composition Methods: Comparisons and Interpretation. *Journal of Diabetes Science and Technology* 2(6):1139-1146.). These measurement methods include, but are not limited to, positron emission tomography (PET), computed tomography (CT), dual energy absorptiometry (DXA) and magnetic resonance (MR). Since 1990, the measurement of central adiposity of large sample populations has primarily been restricted to cost and time expensive CT (Fox C S, Massaro J M, Hoffmann U et al. Abdominal visceral and subcutaneous adipose tissue compartments: association with metabolic risk factors in the Framingham Heart Study. Circulation 116:39-48, 2007; Liu J, Fox C S, Hickson D A, May W D, Hairston K G, Carr J J, Taylor H A. Impact of abdominal visceral and subcutaneous adipose tissue on cardiometabolic risk factors: the Jackson Heart Study. J Clin Endocrinol Metab 95: 5419-5426, 2010.), and to a lesser degree MR (Neeland I J, Turer A T, Ayers C R, Powell-Wiley T M, Vega, G L Farzaneh-Far R, et al. Dysfunctional Adiposity and the Risk of Prediabetes and Type 2 diabetes in Obese Adults. JAMA. 2012; 308(11): 1150-1159.). Following recent technological advancements, lower cost DXA systems have been validated for the measurement of whole body and central adiposity (Kaul S, Rothney M P, Peters D M, et al. Dual-energy X-ray absorptiometry for quantification of visceral fat. Obesity 2012; Doi:10.1038: 1-6.). Through this recent advancement, the cost and time expense associated with medical imaging has been mitigated, but not eliminated. Though reliable, medical imaging technologies are cost expensive, require medical referrals for access and can expose patients to harmful ionising radiation. With reference to an ideal body composition measurement tool, as depicted in FIG. 1, medical imaging techniques are accurate (102), but not affordable (103), nor accessible (101).

Indirect body composition estimation methods like body mass index (BMI), waist circumference (WC), waist-to-hip circumference ratios (WHR) and body impedance analyses (BIA) are cost effective and accessible, however they are met with high levels of measurement error. The reason is because all indirect estimation methods make multiple assumptions associated with body tissue densities, distributions and water concentration(s) (Duren et al., 2008). These assumptions make these methods particularly erroneous among obese, elderly and pathological populations, which ironically are the population cohorts most agencies are trying to identify and treat. It is the combination of these factors that severely limit indirect body composition methods as effective measurement tools for the management of chronic health and musculoskeletal disorders. In the context of an ideal body composition measurement tool, indirect body composition estimation methods are affordable (103) and accessible (101), but not accurate (102).

Although it is well established that BMI is not an accurate representation of an individual's body composition, and in turn a relatively poor measure for the assessment of an individual's chronic health (Bray et al. (2008). Relation of central adiposity and body mass index to the development of diabetes in the Diabetes Prevention Program.) and mortality (Pischon et al., 2008) risk, BMI has still been a common measurement tool within population-based research studies and the insurance sectors. It is also common for self-reported height and weight measures to be used for BMI calculations, which adds even more measurement uncertainty to an already inaccurate measurement. When self-reported height and weight is used for the calculation of an individual's BMI, misclassifications occur at a probability of 22.4% for men and 18.0% for women (Spencer et al. (2001). Validity of self-reported height and weight in 4808 EPIC-Oxford participants. Public Health Nutrition: 5(4), 561-565). For population researchers and insurers who still rely on BMI as a key measurement, an automated and accurate method to estimate and verify an individual's self-reported height and weight from a measurement tool that is accurate, accessible and affordable, would add significant value to population-based research and the insurance sectors.

Since the year 2000, researchers have attempted to bridge the nexus between measurement affordability, accessibility and accuracy by incorporating measurement information derived from high precision 3D surface scanners. What is interesting about this approach is that the 3D human body can be segmented using software that is manually guided by the user into multiple regions (i.e., upper/middle/lower torso, arm, leg, etc.) and a series of linear measures, circumferences, surfaces or volumes. From here a wide variety of volume, surface area, circumference and linear measurements and measurement ratios can be calculated.

Using linear regression methods, 3D surface scanner measurements and measurement ratios are combined with participant characteristic (height, weight, gender, age) information to estimate body composition variables calculated from in-vivo medical imaging technologies. There have been many regression equations published in the literature using these techniques. Two of the most notable equations are those published by Lee et al. (Lee et al. (2014). Predictive Equations for Central Obesity via Anthropometrics, Stereovision Imaging and MRI in Adults.) and Ng et al. (Ng et al. (2016). Clinical anthropometrics and body composition from 3D whole-body surface scans.), who have predicted total body adiposity ($R^2$=0.95) and abdominal adiposity ($R^2$=0.79-0.94) with high accuracy. Visceral fat estimation, which is a key variable for the classification of an individual's health risk has been met with moderate levels of accuracy ($R^2$=0.72-0.75) (Lee et al., 2014; Ng et al., 2016).

This use of 3D surface scanners with regression is met with five notable limitations, as follows. 1) Moderately expensive high precision 3D body surface scanners, within specialized testing environments, are required to obtain a 3D body model of an individual. 2) These methods require the manual handling of the scanned 3D data, limiting its application to general or untrained users. 3) The application of regression-based computational models is in most instances limited to the homogeneous test populations it was developed from; this is generally due to low statistical power and model specification (i.e., over/under-fitting) (McLean, D., Redfern, D., and Pyper, K. (2014). A Survey of Regression Methods for Proxy Functions. Moody's Analytics Research. Consultancy report: B&H Research Insurance ERS.). 4) The segmenting of an individual's body volumes is not guided by an individual's anatomy (i.e., joint centres and anatomical landmarks); instead simple shapes and volumes are fit or registered to an individual's 3D volumetric data. 5) These 3D volumetric and regression-based methods are still not capable of predicting the critical health risk variable from the predicted visceral fat with the levels of accuracy required for medical and which would be an $R^2$>0.90. Considering these limitations together, and with reference to an ideal body composition measurement tool, 3D scanning methods with regression are accurate (102) for a limited size of populations, but not all body composition variables, moderately affordable (103) and moderately accessible (101). Most importantly, the best accuracy reported (e.g. for visceral fat) is for those methods based on either cross-validation type of analysis or where the accuracy is reported based on actual fitted data or trained data, hence the accuracy for any unseen data subjects would be lower than those reported. This is not intentional by the current art but it is due to the lack of larger data size, which is ideally needed for an accurate analysis and modeling of a human population or part of it.

Farahbakhshian et al (Naked Labs) under Patent Application, Publication No. US2018/0137640 A1 have attempted to address the issues of affordability (103) and accessibility (101) by designing a 3D scanner which is moderately affordable, however accuracy of the actual 3D scan can be affected when it comes to the stitch of a rotating deformable, breathable shape like the human body, and estimates of body composition are limited to accurate global volumetric measurements combined with publicly available linear regression equations, for instance, Farahbakhshian et al discuss using either the Siri or Brozak equations to estimate body composition which were developed over a century ago. Furthermore, calculated volumes are not physically meaningful as they were not constrained by any anatomically or physical valid bone joints.

Select Research Limited developed, and disclosed under U.S. Pat. No. 8,374,671 B2 and EP 1 993 443 B1, a laboratory based system which used multiple pre-calibrated cameras to create a visual hull of a person. The hull is then manually cleaned and annotated by an expert and then processed through a software program to split it into different layers of volumes. Their approach combines linear regression methods with 3D volumetric measurements and participant characteristic information to estimate an individual's in-vivo body composition and focuses on the ratios of volumes of parts of the body to estimate health risk. This approach was widely and commonly used and published by many scientists in the same field, the main contribution made by Select Research Limited in the above mentioned patents was the scanning system named body volume index scanner. Like numerical integration errors, these body volumes or geometric shapes are not accurate, and are not able to fit the subtle individualised nuances of the human form and are again not physically meaningful as they were not constrained by any anatomically or physically valid bones or joints of the subject being examined.

The limitations of linear regression and the use of 3D scanner methods including the one by Select Research Limited described above are twofold in that: i) the requirement to use a 3D scanner makes these methods only moderately affordable and accessible; and ii) the use of linear regression-based equations combined with body volume limits their accuracy when applied to heterogenous populations. Furthermore, linear regression has limited degrees of freedom to model infinite shape and composition variations in human bodies across the globe. Moreover, none of the existing regression based inventions for body composition, reinforce the anatomical information, nor an anatomically valid body segment or the actual human shape variations including shapes features in their technology, all of which are considered in embodiments of the present invention disclosed herein.

Given the limited accuracy and the complex setups required for existing arts to deliver, therefore, an individual, insurance companies, government agencies, health care providers and others are still left without an affordable ideal body composition monitoring tool for the effective monitoring and/or treatment of chronic health, musculoskeletal disorders as well as more positively influence premature mortality.

It is against this background that the present invention has been developed.

SUMMARY OF THE INVENTION

It is an object of the present invention to overcome or ameliorate at least one or more of the disadvantages of the prior art, to provide a useful alternative, or to provide consumers, government agencies and health care providers with an informed or commercial choice.

Other objects and advantages of the present invention will become apparent from the following description, taken in connection with the accompanying drawings, wherein, by way of illustration and example, a preferred embodiment of the present invention is disclosed.

According to a first broad aspect of the present invention, there is provided a device for analysing a body, the device comprising:

a controller;

storage storing electronic program instructions for operating the controller; and an input means;

wherein the controller is operable, and guided by instructions of the electronic program, to:

receive input via the input means, the input comprising at least one representation of the body;

process the input to conduct an analysis of the body and generate an output on the basis of the analysis, the processing comprising using a database; and communicate the output.

The representation may be in the form of numbers and/or text and/or data and/or images of any type.

Using the database may comprise accessing and/or interrogating the database.

Optionally, the system comprises a display for displaying a user interface, and the controller is operable, under control of the electronic program instructions, to communicate the output by displaying the output via the display. In this manner, a visualization of the analysis via at least one of text, images, meshes, 3D, videos, icons, virtual reality, and graphs, may be depicted.

Optionally, the device is an implementation of a system.

Optionally, the input comprises details of the body. The details may comprise data and/or information of, associated with, and/or related to, the body. The data and/or information may be obtained by one or more of retrieving, receiving, extracting, and identifying it, from one or more sources.

Optionally, the body is a human body, or one or more parts thereof. In such a case, where the human body is that of an individual person, the output may comprise an estimate of the individual person's 3D body shape and at least one of its associated anthropometry, body composition, and health and wellness risks. The output may comprise an estimate of the individual person's: shape, physical, and ecological characteristics and/or at least one three dimensional (3D) shape and its associated anthropometry, body composition, and health and wellness risks.

Optionally, the body is a body of a living thing, or one or more parts thereof.

Optionally, the body is a body of a non-living thing, or one or more parts thereof.

Optionally, the body is a human body.

The input means may comprise at least one sensor, which may be part of a sensor system or a set of sensors.

Optionally, the representation comprises a visual, non-visual, and/or non-visible representation of the body, which may comprise imagery of the body. In such an implementation, at least one sensor may comprise an imaging means operable to capture the visual, non-visual, and/or non-visible representation of the body. The imaging means may be a digital camera. A non-visual representation may mean data that cannot be visualised such as, for example, floating numbers of matrices or vectors of the body.

Individual sensors within the set of sensors may comprise: a motion sensor; a gyroscope sensor; a gravity sensor, an infra-red sensor; a depth sensor; a three dimensional imaging sensor; an inertial sensor; a Micro-Electromechanical (MEMS) sensor; an imaging means; an acceleration sensor; an orientation sensor; a direction sensor; a position sensor; and a light source sensor.

Optionally, the representation comprises one or more visual, non-visual, or non-visible representations of the body. In such an embodiment, the one or more sensors, where provided, may comprise one or more imaging means operable to capture the one or more visual, non-visual, and/or non-visible representations of the body. Furthermore, the one or more sensors may comprises an orientation sensor operable to provide orientation data for use during capture of the one or more visual, non-visual, and/or non-visible representations of the body to facilitate alignment thereof to a plane for increased accuracy.

Optionally, the body belongs to a category and/or a group and/or a class.

In such a case, the database may comprise details of a plurality of different bodies belonging to the same, and/or a similar, category and/or group and/or class to that of the body being analysed. The details may comprise data and/or information of, associated with, and/or related to, each body of the plurality of different bodies.

Where the category and/or group and/or class comprises humans, the data and/or information may comprise, for each of a plurality of human participants contributing details of their respective bodies to the database, one or more of human medical imaging, body composition, anthropometry, participant characteristics, participant attributes, medical physiology, and epidemiological information, which has been collected whilst collecting, and is linked to, a representation of the respective body of each participant.

Where the category and/or group and/or class comprises humans, the data and/or information may comprise, for each of a plurality of human participants contributing details of their respective bodies to the database, one or more of human videos, photos, full and/or partial body shapes or surface scans, medical imaging, body composition, anthropometry, participant characteristics, participant attributes, medical physiology, and epidemiological information, which has been collected whilst collecting, and is linked, and/or registered, and/or aligned, and/or matched to, a unified representation of the respective body of each participant.

Optionally, collecting of the details and of the representation of the respective body of each participant comprises capturing the details and the representation of the body of each participant contributing to the database in accordance with quality assurance protocols and pre-processing processes and steps.

Optionally, the collecting of the details and of the representation of the respective body of each participant preferably occurs simultaneously and in parallel, but may be done at different times. This may be done for each participant.

Optionally, additional data are collected at different time intervals to enable the creation and/or development of temporal modeling of participant (human) shape(s) and data gathered over time, and to derive statistically meaningful diagnostic trackers, and to achieve a physically meaningful risk analysis and/or trend.

The data and/or information may comprise intrinsic and/or extrinsic data and/or information of sensory input or devices.

Optionally, the details of contributors to the database are captured according to quality assurance and pre-processing steps and protocols.

Optionally, collecting of the details and of the representation of the respective body of each participant comprises capturing the details and the representation of the body of each participant contributing to the database in accordance with quality assurance and pre-processing steps.

The quality assurance and pre-processing steps may comprise techniques related to a capturing phase of human imagery which may be in the form of an image or images, videos or video frames, 2.xD images including depth images and/or 3D body scans for the database.

The quality assurance and pre-processing steps may comprise techniques related to a capturing phase of anthropometry data for the database.

The quality assurance and pre-processing steps may comprise techniques related to a capturing phase of dynamic data for the database.

Optionally, the processing comprises actions performed by statistical analysis and/or at least one computer vision (CV), machine learning (ML), and/or artificial intelligence (AI) model.

The actions may comprise at least one of:
analysing the collected data and imageries using advance multi-dimensional statistical techniques and/or machine learning techniques and/or AI techniques and excluding those identified as outliers;
classifying, clustering, grouping data and imageries into one or more of groups, regions, types, and categories based on one or more labeling mechanism of the data type and/or an associated output linked to the data type;
estimating features and/or land marks and/or anatomically relevant land marks and/or key points and/or joint centres and/or bone links from the imagery of the body;
estimating body part segmentation from the imagery of the body constrained by image features and/or anatomical features extracted from medical imaging and establishing 2D and/or 3D body parts and/or 2D and/or 3D regions of interest (ROI); and
extracting 2D and/or 3D image and shape features and labeled image(s) segments and/or image clusters and body shapes.

The actions may comprise at least one of:
analysing the collected data and imageries using advance multi-dimensional statistical techniques and/or machine learning techniques and/or AI techniques and exclude those identified as outliers;
classifying, clustering data and imageries into one or more of groups, regions, types, characteristics and categories based on one or more labeling and/or annotation mechanism of the data type and/or an associated output linked to the data type;
estimating salient features and/or land marks including anatomically relevant land marks and/or key points and/or joint centres and/or bone links from any type of imagery of the body;
identifying and segmenting the body from cluttered backgrounds in imagery;
estimating body part segments from the imagery of the body constrained by anatomical features extracted from medical imaging and establishing regions of interest (ROI); and
extracting image or generally shape features and labeled image(s) segments and/or image clusters and estimate their correspondence with the body data.

The processing may comprise a processing technique where CV/ML/AI models estimate subject or user specific anatomically relevant landmarks, bone links, and/or joint centres from the human imagery data; videos, 2.xD or 3D images.

The processing may comprise a processing technique where ML/AI models estimate body part segmentation from the human imagery including 3D imageries constrained by anatomical features extracted from medical imaging and establish subject or user specific 2D and/or 3D regions of interest.

The processing may comprise a processing technique where ML/AI models extract 2D and/or 3D image and shape features and labeled image(s) segments and/or image clusters and the corresponding 2D and/or 3D body shapes and/or body segments.

The processing may comprise a processing technique where ML/AI models link, associate, and/or co-register human imagery data, participant characteristic and attributes, and medical physiology data with in-vivo measures of an individual's body composition and physical anthropometry measures. Such processing may comprise using at least an algorithm trained to accurately estimate a variety of body composition and anthropometry measures from individual or user specific human imagery data, participant characteristics and attributes, and medical physiology data.

The processing may comprise a processing technique where ML/AI models link/learn wellness scores/activities with the database, 2D and/or 3D body images, shapes, body parts, body segments and/or medical data.

The processing may comprise a step where estimated body composition and anthropometry of the user are displayed as output and/or saved as a file and/or transmitted over a secure web link.

The processing may comprise a step where current and historical body composition and body measurements are retrieved from the device and/or a storage in the cloud and/or a server then tracked and displayed over time as an output.

The processing may comprise a step where various health and wellness indicators and risk factor comparisons are provided as an output, which may include without limitation, on or more of the following:

i) estimations of measurement such as total or segment body fat, lean mass, visceral fat, android fat, gynoid fat, bone mass;

ii) classifications of a measurement such as those for body fat e.g. lean, normal, overweight and obese; and for visceral fat e.g. low risk, normal risk, elevated risk, high risk;

iii) comparisons to normative population distributions contained within the database;

iv) estimates based on trained ML/AI models and a predictive risk approach or equations for a particular user of:
  a. the risk that the user is prediabetic;
  b. their increased risk for the user of chronic health diseases, musculoskeletal disorders, mortality and falls event risks;

v) an approach to detect sarcopenia either directed by the user or triggered by an estimated low muscle lean mass ratio to height or other relevant anthropometric measurement.

The processing may comprise an approach where tailored interventions are output and displayed for implementation. This may beneficially promote positive health behaviour change, which may be translated to improved health and wellness outcomes for the individual.

The optional display, user interface and input means may be integrated, in a touchscreen for example. Alternatively, they may be discrete.

In an embodiment, the input comprises user instructions which are input by a user via the input means. The user instructions may comprise a command to perform an action, in which case the controller is operable, under control of the electronic program instructions, to perform the action according to the received user instructions.

In an embodiment, the electronic program instructions comprise software. The device may be a mobile communication device, in which case it may comprise a smartphone, notebook/tablet/desktop computer, a camera, or portable media device, having the software installed thereon. The software may be provided as a software application downloadable to the device, and/or running on servers and/or the cloud as a service.

Preferably, operations performed by the device occur automatically, without requiring human intervention.

According to a second broad aspect of the present invention, there is provided a method for analysing a body, the method comprising:

storing electronic program instructions for controlling a controller; and controlling the controller via the electronic program instructions, to:

receive input via the input means, the input comprising at least one representation of the body;

process the input to conduct an analysis of the body and generate an output on the basis of the analysis, the processing comprising accessing a database.

The representation may comprise a visual representation comprising imagery of the body, and/or a non-visual representation, meaning data that cannot be visualised.

The processing may comprise actions performed by at least one computer vision (CV), machine learning (ML), and/or artificial intelligence (AI) model.

Optionally, the body being analysed belongs to a category and/or a group and/or a class. In such a case, the database may comprise details of a plurality of different bodies belonging to the same, and/or a similar, category and/or group and/or class to that of the body being analysed, the details comprising data and/or information of, associated with, and/or related to each body of the plurality of bodies.

Where the category and/or group and/or class comprises humans, the data and/or information may comprise, for each of a plurality of human participants contributing details of their respective bodies to the database, one or more of human videos, photos, full and/or partial body shapes or surface scans, medical imaging, body composition, anthropometry, participant characteristics, participant attributes, medical physiology, and epidemiological information, which has been collected whilst collecting, and is linked, and/or registered, and/or aligned, and/or matched to, a unified representation of the respective body of each participant.

Optionally, the collecting of the details and of the representation of the respective body of each participant occurs simultaneously and in parallel, but may be done at different times.

Optionally, additional data are collected at different time intervals to enable the creation and/or development of temporal modeling of participant (human) shape(s) and data gathered over time, and to derive statistically meaningful diagnostic trackers, and to achieve a physically meaningful risk analysis and/or trend.

Optionally, collecting of the details and of the representation of the respective body of each participant comprises capturing the details and the representation of the body of each participant contributing to the database in accordance with quality assurance protocols and pre-processing processes and steps.

The processing may comprise actions performed by statistical analysis and/or at least one computer vision (CV), machine learning (ML), and/or artificial intelligence (AI) model.

The actions may comprise at least one of:

analysing the collected data and imageries using advance multi-dimensional statistical techniques and/or machine learning techniques and/or AI techniques and exclude those identified as outliers;

classifying, clustering data and imageries into one or more of groups, regions, types, characteristics, and categories based on one or more labeling and/or annotation mechanism of the data type and/or an associated output linked to the data type;

estimating salient features and/or land marks including anatomically relevant land marks and/or key points and/or joint centres and/or bone links from any type of imagery of the body;

identifying and segmenting the body from cluttered backgrounds in imagery;

estimating body part segments from the imagery of the body constrained by anatomical features extracted from medical imaging and establishing regions of interest (ROI); and extracting image or generally shape features and labeled image(s) segments and/or image clusters and estimate their correspondence with the body data.

The method may further comprise controlling the controller, via the electronic program instructions, to communicate the output by displaying the output via a display. In this manner, a visualization of the analysis via at least one of text, images, meshes, 3D, videos, icons, virtual reality, and graphs, may be depicted.

The method may further comprise communicating the output. The communicating may comprise displaying the output via a display and/or as a readable data either on files or printed.

Optionally, the body is that of an individual person, and the output comprises an estimate of the individual person's 3D body shape and at least one of its associated anthropometries, body composition, and health and wellness risks. The output may comprise an estimate of the individual person's: shape, physical, and ecological characteristics and/or at least one three dimensional (3D) shape and its associated anthropometry, body composition, and health and wellness risks.

According to a third broad aspect of the present invention, there is provided a computer-readable storage medium on which is stored instructions that, when executed by a computing means, causes the computing means to perform the method according to the second broad aspect of the present invention as hereinbefore described.

According to a fourth broad aspect of the present invention, there is provided a computing means programmed to carry out the method according to the second broad aspect of the present invention as hereinbefore described.

According to a fifth broad aspect of the present invention, there is provided a data signal including at least one instruction being capable of being received and interpreted by a computing system, wherein the instruction implements the method according to the second broad aspect of the present invention as hereinbefore described.

According to a sixth broad aspect of the present invention, there is provided a system for analysing a body comprising a device according to the first broad aspect of the present invention as hereinbefore described.

One embodiment provides a computer program product for performing a method as described herein.

One embodiment provides a non-transitive carrier medium for carrying computer executable code that, when executed on a processor, causes the processor to perform a method as described herein.

One embodiment provides a system configured for performing a method as described herein.

BRIEF DESCRIPTION OF THE DRAWINGS

Notwithstanding any other forms which may fall within the scope of the present invention, in order that the invention may be more fully understood and put into practice, preferred embodiments of the invention will now be described, by way of example only, with reference to the accompanying drawings, in which:

FIG. 1 depicts an ideal body composition measurement model, showing the nexus of what is needed for an ideal body composition measurement tool;

FIGS. 2 and 3 depict a flow chart of user completed actions of a first embodiment of a method, using a first embodiment of a system, in accordance with aspects of the present invention, providing an overview of a device to estimate body composition and health and wellness risks from human imagery;

FIG. 4 depicts a general overview of steps involved for data collection and processing for a BCT database 40 of the system of FIGS. 2 and 3;

FIG. 5 depicts a more detailed description of the data collected for the BCT database of the system of FIGS. 2 and 3;

FIGS. 6a and 6b depict a general overview of data, medical imagery, and human imagery quality control procedures of the system of FIGS. 2 and 3;

FIG. 7 depicts a general overview of anatomical landmark identification from medical images of a process of the system of FIGS. 2 and 3. Joint centre positions can be observed on the right. Regions of interest can be observed on the left;

FIG. 8 depicts an overview of training of a ML/AI algorithm of the system of FIGS. 2 and 3 to estimate joint centres;

FIG. 9 depicts defined Regions of Interest and anatomical landmarks;

FIG. 10 depicts a general overview of a predictive health risk equation for prediabetes, chronic health disease and mortality of the system of FIGS. 2 and 3;

FIG. 11 depicts an example of a calculation of a Relative Health Risk Calculator of the system of FIGS. 2 and 3;

DEFINITIONS

Figure 3:
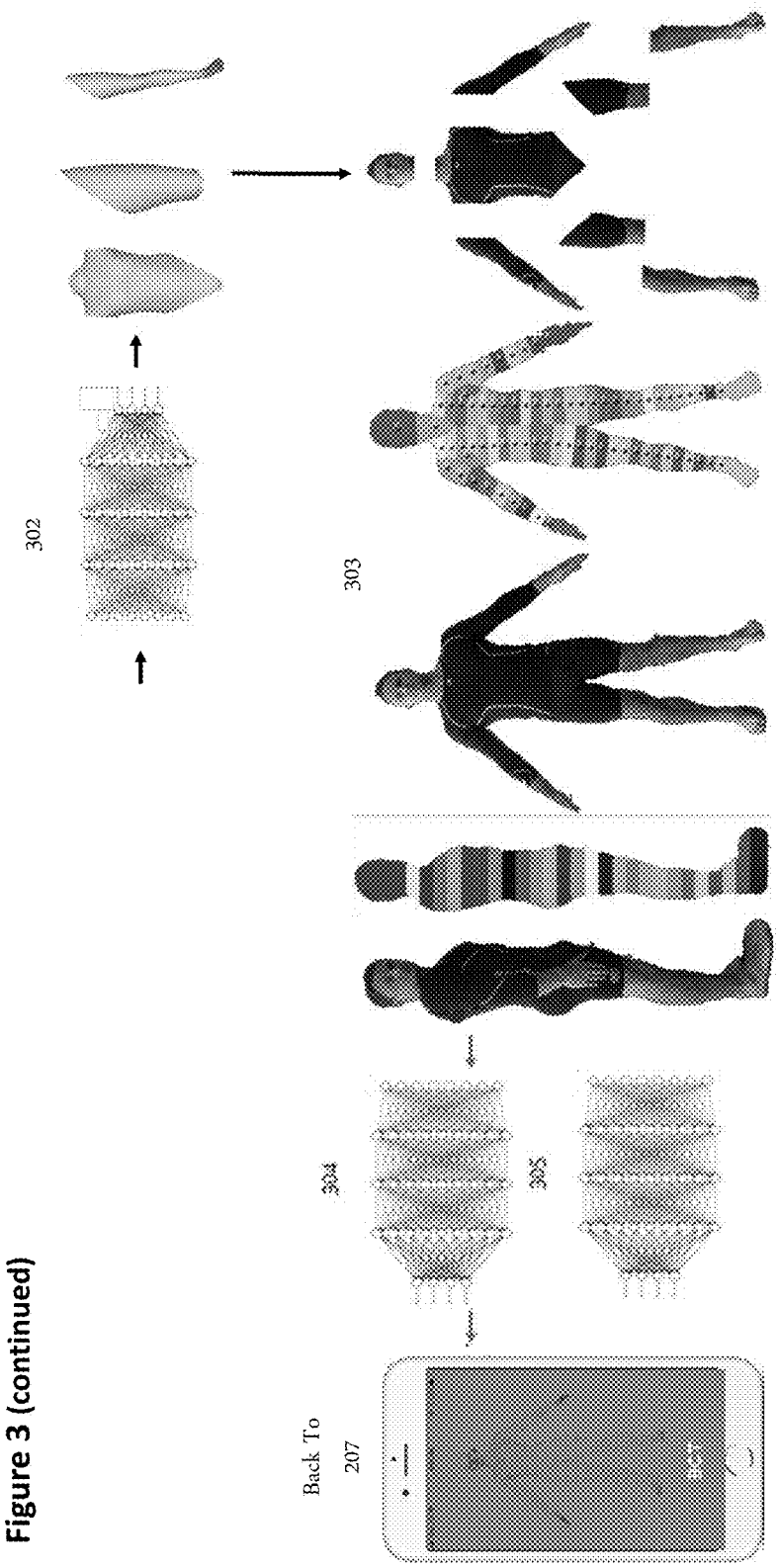

The following definitions are provided as general definitions and should in no way limit the scope of the present invention to those terms alone, but are put forth for a better understanding of the following description.

Unless defined otherwise, all technical and scientific terms used herein have the same meaning as commonly understood by those of ordinary skill in the art to which the invention belongs. It will be further understood that terms used herein should be interpreted as having a meaning that is consistent with their meaning in the context of this specification and the relevant art and will not be interpreted in an idealized or overly formal sense unless expressly so defined herein. For the purposes of the present invention, additional terms are defined below. Furthermore, all definitions, as defined and used herein, should be understood to control over dictionary definitions, definitions in documents incorporated by reference, and/or ordinary meanings of the defined terms unless there is doubt as to the meaning of a particular term, in which case the common dictionary definition and/or common usage of the term will prevail.

For the purposes of the present invention, the following terms are defined below.

The articles "a" and "an" are used herein to refer to one or to more than one (i.e. to at least one) of the grammatical object of the article. By way of example, "an element" refers to one element or more than one element.

The term "about" is used herein to refer to quantities that vary by as much as 30%, preferably by as much as 20%, and more preferably by as much as 10% to a reference quantity. The use of the word 'about' to qualify a number is merely an express indication that the number is not to be construed as a precise value.

Throughout this specification, unless the context requires otherwise, the words "comprise", "comprises" and "comprising" will be understood to imply the inclusion of a stated step or element or group of steps or elements but not the exclusion of any other step or element or group of steps or elements.

Any one of the terms: "including" or "which includes" or "that includes" as used herein is also an open term that also means including at least the elements/features that follow the term, but not excluding others. Thus, "including" is synonymous with and means "comprising".

In the claims, as well as in the summary above and the description below, all transitional phrases such as "comprising," "including," "carrying," "having," "containing," "involving," "holding," "composed of," and the like are to be understood to be open-ended, i.e., to mean "including but not limited to". Only the transitional phrases "consisting of" and "consisting essentially of" alone shall be closed or semi-closed transitional phrases, respectively.

The term, "real-time", for example "displaying real-time data," refers to the display of the data without intentional delay, given the processing limitations of the system and the time required to accurately measure the data.

The term. "near-real-time", for example "obtaining real-time or near-real-time data" refers to the obtaining of data either without intentional delay ("real-time") or as close to real-time as practically possible (i.e. with a small, but minimal, amount of delay whether intentional or not within the constraints and processing limitations of the of the system for obtaining and recording or transmitting the data.

Although any methods and materials similar or equivalent to those described herein can be used in the practice or testing of the present invention, preferred methods and materials are described. It will be appreciated that the methods, apparatus and systems described herein may be implemented in a variety of ways and for a variety of purposes. The description here is by way of example only.

As used herein, the term "exemplary" is used in the sense of providing examples, as opposed to indicating quality. That is, an "exemplary embodiment" is an embodiment provided as an example, as opposed to necessarily being an embodiment of exemplary quality for example serving as a desirable model or representing the best of its kind.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The phrase "and/or", as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one", in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

For the purpose of this specification, where method steps are described in sequence, the sequence does not necessarily mean that the steps are to be carried out in chronological order in that sequence, unless there is no other logical manner of interpreting the sequence.

In addition, where features or aspects of the invention are described in terms of Markush groups, those skilled in the art will recognise that the invention is also thereby described in terms of any individual member or subgroup of members of the Markush group.

DESCRIPTION OF EMBODIMENTS

It should be noted in the following description that like or the same reference numerals in different embodiments denote the same or similar features.

In FIGS. 2 and 3, there is depicted actions performed during use of a first embodiment of a system 10 depicted in FIG. 2 (System) for analysing a body using a device 12 in accordance with aspects of the present invention.

In the embodiment described, the body is a body 14 of a human 16 (being a user of the system 10).

The present invention will be described with particular reference to analysing a human body to provide an estimation of an individual's three-dimensional (3D) body shape and its associated body composition and health and wellness risks using (without limiting the generality) one or more of images and/or features and/or any type of data, representation, or information that is capable of one or more of defining, explaining or describing an ecologically and physically valid model or analogy of the body shape and its molecular compositions. Accordingly, the embodiment of the system 10 is for estimating shape, body compositions, and health risk from human imagery.

That said, it will be appreciated that the invention may be used in respect of bodies of other things and for performing an analysis for additional and/or alternative purposes or objectives.

It will be appreciated that the invention is not limited in regard to the body analysed, or the purpose for which or the way in which it is analysed, and in alternative embodiments, the invention may be applied to analysing bodies of additional and/or alternative things, for additional and/or alternative purposes to those described. Depending on the implementation, the body may be a body of a living thing, or one or more parts thereof, or a body of a non-living thing, or one or more parts thereof. Embodiments of the invention are particularly applicable to analysing bodies of things within which there is variation between the body of one and another, such as animals, including livestock, as well as humans (as in the described embodiment).

As will be described in further detail, the embodiment of the invention comprises a system 10 implementing a method for estimating an individual's three-dimensional (3D) body shape and its associated body composition and health and wellness risks from human imagery that the inventors have developed. The method involves the collection of a unique diverse global multi-dimensional database of details of participant, or contributing, human bodies, including human imagery, medical imaging, medical physiology, participant characteristics and attributes, anthropometry and epidemiology data using various data capturing devices. Novel and advanced statistical methods, Computer Vision (CV), Machine learning (ML) and Artificial Intelligence (AI) approaches then use this database to understand human imagery, extract distinctive features and characteristics from them, and link them to human body shape, body composition, medical physiology and health and wellness risks. In embodiments, entire processes facilitating the above are performed offline under strict quality assurance protocols to produce a standalone system or an application that can be utilized by the general public and scientists. The invented system 10, of the embodiment, provides an affordable and accessible method to estimate body composition and health and wellness risks within the medical and health, fitness, insurance and government sectors.

Advanced machine learning techniques used by embodiments of the invention may include Convolution Neural Network (CNN) technology.

The protocols and processes developed by the inventors in the present invention allow it to deal with this complex type of human data type and structure, in the embodiment.

Conceptually, the embodiment of the invention may be seen to comprise six broad levels. As will be described in further detail, some levels are performed in an off-line phase to facilitate actions including those to capture, control, handle, process and link all types of collected data required to produce or implement the invention in the embodiment, others are executed during an online phase to facilitate actions in which a subset of the data, such as a human image(s), are captured, processed to and output or used to predict other subsets (e.g. outputting body composition).

Regarding the six levels, a first, offline, level relates to the collection of a large and diverse database across the world of details of participant, or contributing, human bodies, including human medical imaging, body composition, anthropometry, physical characteristics and attributes, and medical physiology and epidemiology data while simultaneously collecting human imagery using various types of data capturing devices. An advantageous feature of the embodiment of the present invention is the provision of a system 10 operable to collect, prepare, analyse, and process a large database of human visual images, medical imaging, body composition, anthropometry, physical characteristics and attributes, medical physiology and epidemiology data while simultaneously collecting human imagery.

A second, offline, level relates to the development of methodological procedures to provide for the reliable and unified collection of the data in the database combined with new and advanced image processing techniques and data quality control procedures to facilitate actions including those to assess, rectify, analyse, prepare and link the collected multi-dimensional data.

A third, offline, level relates to the development of Computer Vision (CV), Machine Learning (ML) and Artificial Intelligence (AI) approaches and models that are operable to facilitate actions including those to study, analyse and link human imagery and the related human features, participant characteristics and medical physiology and link them to body composition data, anatomical bone joints (from medical images), anatomically valid body parts segments (from medical images) and 3D body shapes (either reconstructed from images or acquired via a 3D shape scanner).

The actions may comprise at least one of:
analysing the collected data and imageries using advance multi-dimensional statistical techniques and/or machine learning techniques and/or AI techniques and excluding those identified as outliers;
classifying, clustering, grouping data and imageries into one or more of groups, regions, types, and categories based on one or more labeling mechanism of the data type and/or an associated output linked to the data type;
estimating features and/or land marks and/or anatomically relevant land marks and/or key points and/or joint centres and/or bone links from the imagery of the body;
estimating body part segmentation from the imagery of the body constrained by image features and/or anatomical features extracted from medical imaging and establishing 2D and/or 3D body parts and/or 2D and/or 3D regions of interest (ROI); and
extracting 2D and/or 3D image and shape features and labeled image(s) segments and/or image clusters and body shapes.

The actions may comprise at least one of:
analysing the collected data and imageries using advance multi-dimensional statistical techniques and/or machine learning techniques and/or AI techniques and exclude those identified as outliers;
classifying, clustering data and imageries into one or more of groups, regions, types, characteristics, and categories based on one or more labeling and/or annotation mechanism of the data type and/or an associated output linked to the data type;
estimating salient features and/or land marks including anatomically relevant land marks and/or key points and/or joint centres and/or bone links from any type of imagery of the body;
identifying and segmenting the body from cluttered backgrounds in imagery;
estimating body part segments from the imagery of the body constrained by anatomical features extracted from medical imaging and establishing regions of interest (ROI); and
extracting image or generally shape features and labeled image(s) segments and/or image clusters and estimate their correspondence with the body data.

It should be appreciated that the CV/ML/AI is not limited in regard to the models of the embodiment described herein, and in alternative embodiments of the invention additional and/or alternative models may be learned and outputs generated according to the body or thing intended to be analysed. The constraints of the learning process may comprise additional and/or alternative training, testing and validation, more or less data, and additional and/or alternative type(s) of data than that of the embodiment described, as appropriate to the implementation of the invention, according to the body or thing intended to be analysed and the decisions to be made.

A fourth, online, level relates to the use of the device 12 to capture input including human imagery and related human features, characteristics and medical physiology. The device 12, in addition to a number of controlling modules and applications integrated with novel CV, ML and AI approaches, is then operable and used to facilitate actions including those to handle and process this imagery to extract distinctive imagery features, landmarks, keypoints (either visible as marker or marker-less i.e. not visible), estimate human joints, bone links, body part segments and reconstruct a valid 3D body shape.

A fifth, online, level relates to the use of additional CV, ML and AI models and approaches (driven by the data and machine learned model trained offline), to facilitate actions including those to process the human imagery and the related human features, participant characteristics, medical physiology and epidemiological data captured and processed online in order to estimate body composition, health and wellness risk and any other parameters in the dataset being collected offline.

A sixth, online level relates to the use of the processed human imagery and the related human features, participant characteristics and medical physiology, three-dimensional (3D) body shape and the estimated body composition data and additional health and wellness data all of which are analysed, studied, and modeled as an output of the fifth level above, to facilitate actions including those to allow the individual to classify, assess and monitor their health and wellness over their lifespan.

Although the present invention will be described with reference to estimating an individual's body composition, anthropometry and health and wellness risk from human imagery data and other individual personal data for the medical and health, fitness, insurance and government sectors; it should be appreciated that it may be used in respect of bodies of other things, and for additional and/or alternative purposes. Additionally, though the embodiment of the present invention implements a link between central (i.e., android, gynoid and visceral fat) and whole-body adiposity and lean muscle mass to an individual's risk of chronic health disease like diabetes, cardiovascular disease, musculoskeletal disorders like frailty and knee and hip joint osteoarthritis as well as prediabetes, premature mortality and sarcopenia, it should be appreciated that a wider range of body composition, anthropometric variables and medical physiology can be estimated and linked to other relevant conditions, disorders or diseases within the medical, health and medical research sectors, which more globally is classified within an individual's health and wellness risk. These body composition, anthropometric variables and medical physiology data include but are not limited to organ tissue, muscle tissue, bone mineral density, blood pressure, heart rate, plasma glucose, HbA1c and other relevant blood/ plasma information, for example.

The device 12 is carried by a person being the user 16.

Figure 12:
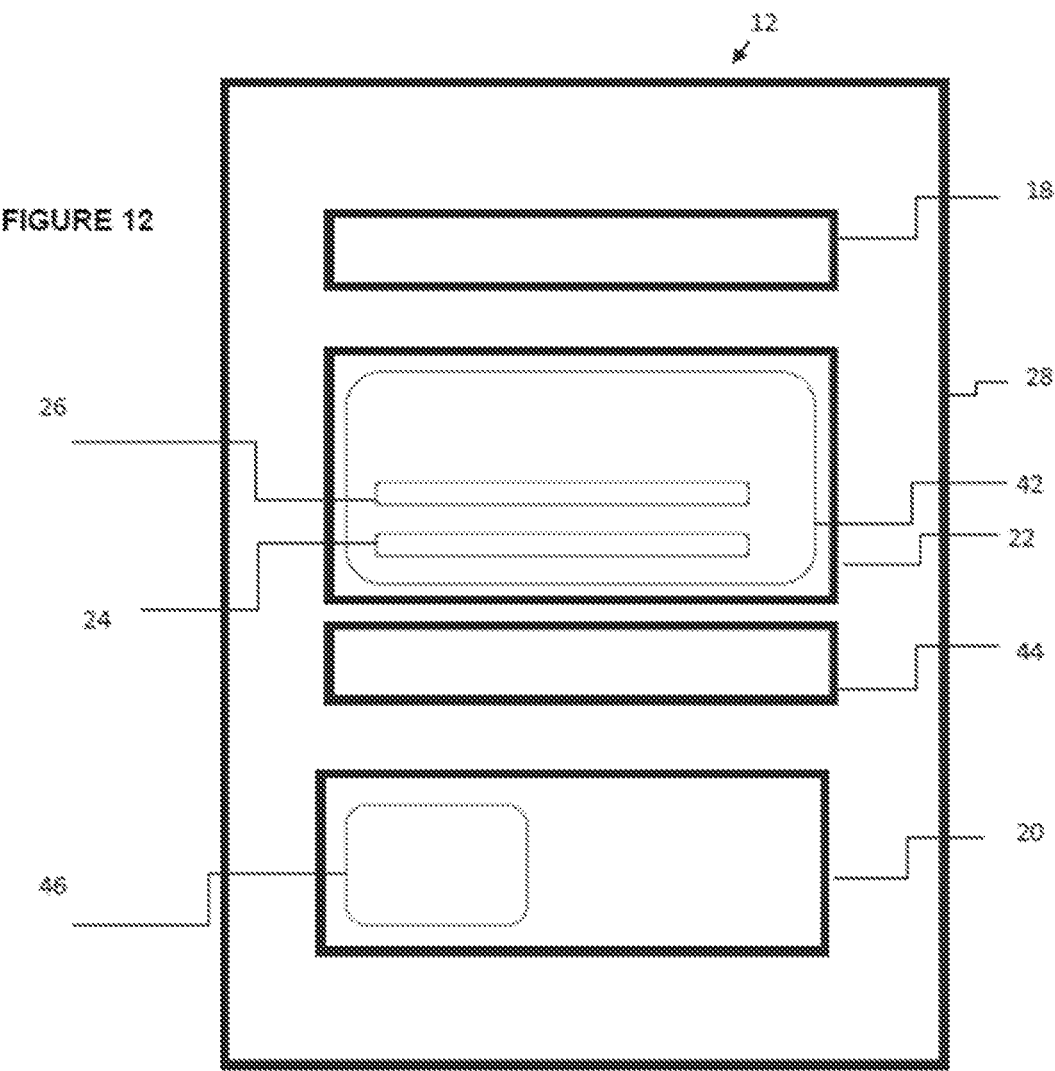
FIG. 12 depicts a schematic diagram of an embodiment of a device in accordance with an aspect of the present invention.

As depicted in FIG. 12, the device 12 comprises a plurality of components, subsystems and/or modules operably coupled via appropriate circuitry and connections to enable the device 12 to perform the functions and operations herein described. The device 12 comprises suitable components necessary to receive, store and execute appropriate computer instructions such as a method for analysing a body in accordance with embodiments of the present invention.

Particularly, and as shown in FIG. 12, the device 12 comprises computing means which in this embodiment comprises a controller 18 and storage 20 for storing electronic program instructions for controlling or operating the controller 18, and information and/or data; a display 22 for displaying a user interface 24; and input means 26; all housed within a container or housing 28.

As will be described in further detail, the controller 18 is operable, under control or otherwise guided by instructions of the electronic program, to: receive input via the input means, the input comprising at least one representation of the body 14; process the input to conduct an analysis of the body and generate an output on the basis of the analysis, the processing comprising using a database; and communicate the output by displaying the output via the display 22.

Particularly, in the embodiment, the controller 18 is operable to control and run applications for estimating shape and health risk from human imagery.

As will be described in further detail, the at least one representation may be in the form of numbers and/or text and/or data and/or images of any type.

Using the database may comprise accessing and/or interrogating the database.

In embodiments of the invention, the input may comprise data and/or information, which may be obtained by one or more of capturing, retrieving, receiving, extracting, and identifying it, from one or more sources. The one or more sources of data may reside on the storage 20, and/or elsewhere, remote from the device 12. The data and/or information may comprise intrinsic and/or extrinsic data and/or information derived from sensory input or devices.

In the embodiment, the body 14 belongs to a category and/or a group and/or a class. The database may comprise details of a plurality of different bodies belonging to the same, and/or a similar, category and/or group and/or class to that of the body being analysed. The details may comprise data and/or information of, associated with, and/or related to, each body of the plurality of different bodies.

Where the category and/or group and/or class comprises humans, as in the embodiment, the data and/or information may comprise, for each of a plurality of human participants contributing details of their respective bodies to the database, one or more of human medical imaging, body composition, anthropometry, participant characteristics, participant attributes, medical physiology, and epidemiological information, which has been collected whilst collecting, and is linked to, a representation of the respective body of each participant.

Where the category and/or group and/or class comprises humans, the data and/or information may comprise, for each of a plurality of human participants contributing details of their respective bodies to the database, one or more of human videos, photos, full and/or partial body shapes or surface scans, medical imaging, body composition, anthropometry, participant characteristics, participant attributes, medical physiology, and epidemiological information, which has been collected whilst collecting, and is linked, and/or registered, and/or aligned, and/or matched to, a unified representation of the respective body of each participant.

The controller 18 comprises processing means in the form of a processor.

The storage 20 comprises read only memory (ROM) and random access memory (RAM).

The device 12 is capable of receiving instructions that may be held in the ROM or RAM and may be executed by the processor. The processor is operable to perform actions under control of electronic program instructions, as will be described in further detail below, including processing/ executing instructions and managing the flow of data and information through the device 12.

In the embodiment, electronic program instructions for the device 12 are provided via a single standalone software application (app) or module which may be referred to as a body analysis app, and/or as a software development kit (SDK) to be included or executed from within other apps, and/or a service running on servers and/or the clouds. In the embodiment described, the app, and/or SDK and/or service is marketed under the trade mark BCT™, and can be downloaded from a website (or other suitable electronic device platform) or otherwise saved to or stored on storage 20 of the device 12 and/or executed via an Application Program Interface (API).

In preferred embodiments of the invention, the device 12 is a mobile communication device and comprises a smartphone such as that marketed under the trade mark IPHONE® by Apple Inc, or by other provider such as Nokia Corporation, or Samsung Group, having Android, WEBOS, Windows, or other Phone app platform. Alternatively, the device 10 may comprise other computing means such as a personal, notebook or tablet computer such as that marketed under the trade mark IPAD® or IPOD TOUCH® by Apple Inc, or by other provider such as Hewlett-Packard Company, or Dell, Inc, for example, or other suitable device.

The device 12 also includes an operating system which is capable of issuing commands and is arranged to interact with the app to cause the device 12 to carry out actions including the respective steps, functions and/or procedures in accordance with the embodiment of the invention described herein. The operating system may be appropriate for the device 12. For example, in the case where the device 12 comprises an IPHONE® smartphone, the operating system may be iOS.

Figure 13:
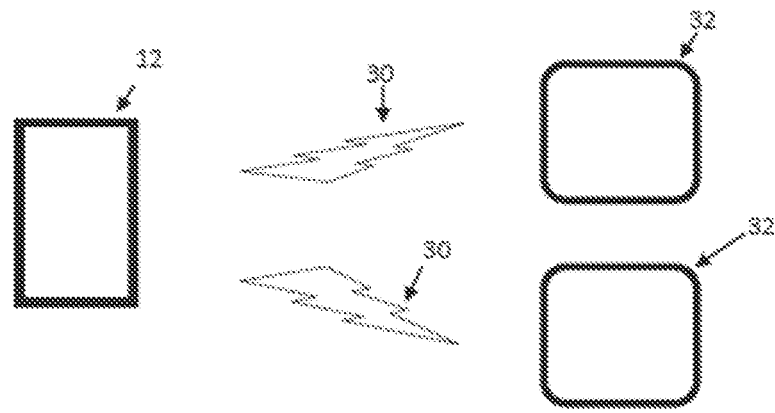
FIG. 13 depicts a simplified system diagram of the system of FIGS. 2 and 3.
Figures 14A, 14B, 14C, 14D:
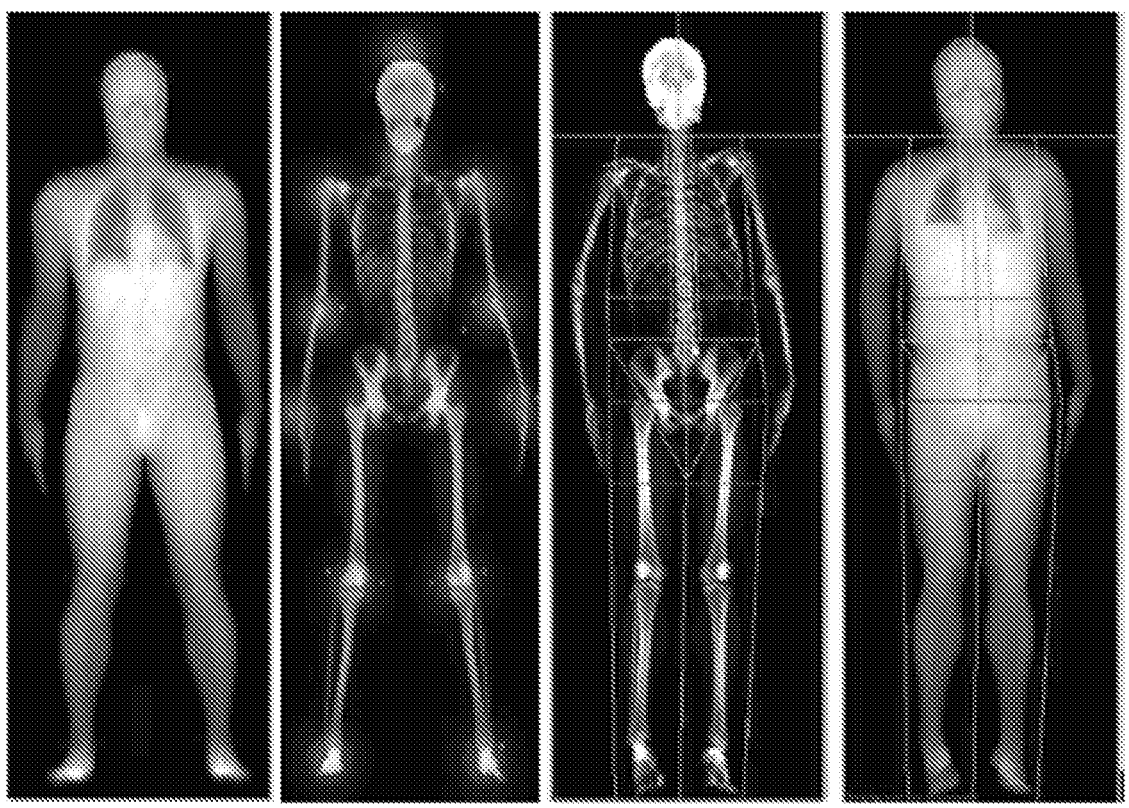
FIGS. 14a, 14b, 14c, and 14d depict example images for training a CV/ML/AI model operable to estimate subject or user specific anatomical information and joints from a human image of the system of FIGS. 2 and 3.

As depicted in FIG. 13, the device 12 is operable to communicate via one or more communications link(s) 30, which may variously connect to one or more remote devices 32 such as servers, personal computers, terminals, wireless or handheld computing devices, landline communication devices, or mobile communication devices such as a mobile (cell) telephone. At least one of a plurality of communications link(s) 30 may be connected to an external computing network through a telecommunications network.

In the embodiment described, the remote devices 32 include other devices 12, owned and/or operated by other persons, as well as a computing system 34 owned and operated by an administrator.

The administrator computing system 34 has the form of a server 36 in the embodiment. The server 36 may be used to execute application and/or system services such as a system and method for analysing a body in accordance with embodiments of the present invention.

In the embodiment, the server 36 is implemented via cloud computing and held on a cloud based platform with appropriate resources and infrastructure. In alternative embodiments, it may be physically located at a centrally managed administration centre.

Similar to the device 12, the infrastructure supporting the server 36 comprises suitable components necessary to receive, store and execute appropriate electronic program instructions. The components include processing means in the form of a server processor, server storage comprising read only memory (ROM) and random access memory (RAM), one or more server input/output devices such as disc drives, and an associated server user interface. Remote communications devices 32 (including the device 12) are arranged to communicate with the server 36 via the one or more communications link(s) 30.

The server 36 is capable of receiving instructions that may be held in ROM, RAM or disc drives and may be executed by the server processor. The server processor is operable to perform actions under control of electronic program instructions, as will be described in further detail below, including processing/executing instructions and managing the flow of data and information through the computing system 34.

The server 36 includes a server operating system which is capable of issuing commands to access a plurality of databases or databanks which reside on the storage device thereof. In the embodiment, two such databases or databanks are provided, comprising: one of registered users (RU) of the system 10, which may be referred to as an RU database 38; and one of the hereinbefore described database, which may be referred to as a BCT database 40. The operating system is arranged to interact with the databases 38 and 40 and with one or more computer programs of a set/suite of server software to cause the server 36 to carry out actions including the respective steps, functions and/or procedures in accordance with the embodiment of the invention described herein.

The app, computer programs of the server software set, and other electronic instructions or programs for the computing components of the device 12 and the server 36 can be written in any suitable language, as are well known to persons skilled in the art. For example, for operation on a device 12 comprising an IPHONE® smartphone, the body analysis app may be written in the Objective-C language. In embodiments of the invention, the electronic program instructions may be provided as stand-alone application(s), as a set or plurality of applications, via a network, or added as middleware, depending on the requirements of the implementation or embodiment.

In alternative embodiments of the invention, the software may comprise one or more modules, and may be implemented in hardware. In such a case, for example, the modules may be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA) and the like.

The respective computing means can be a system of any suitable type, including: a programmable logic controller (PLC); digital signal processor (DSP); microcontroller; personal, notebook or tablet computer, or dedicated servers or networked servers.

The respective processors can be any custom made or commercially available processor, a central processing unit (CPU), a data signal processor (DSP) or an auxiliary processor among several processors associated with the computing means. In embodiments of the invention, the processing means may be a semiconductor based microprocessor (in the form of a microchip) or a macroprocessor, for example.

In embodiments of the invention, the respective storage can include any one or combination of volatile memory elements (e.g., random access memory (RAM) such as dynamic random access memory (DRAM), static random access memory (SRAM)) and non-volatile memory elements (e.g., read only memory (ROM), erasable programmable read only memory (EPROM), electronically erasable programmable read only memory (EEPROM), programmable read only memory (PROM), tape, compact disc read only memory (CD-ROM), etc.). The respective storage may incorporate electronic, magnetic, optical and/or other types of storage media. Furthermore, the respective storage can have a distributed architecture, where various components are situated remote from one another, but can be accessed by the processing means. For example, the ROM may store various instructions, programs, software, or applications to be executed by the processing means to control the operation of the device 12 and the RAM may temporarily store variables or results of the operations.

The use and operation of computers using software applications is well-known to persons skilled in the art and need not be described in any further detail herein except as is relevant to the present invention.

Furthermore, any suitable communication protocol can be used to facilitate connection and communication between any subsystems or components of the device 12, any subsystems or components of the server 36, and the device 12 and server 36 and other devices or systems, including wired and wireless, as are well known to persons skilled in the art and need not be described in any further detail herein except as is relevant to the present invention.

Where the words "store", "hold" and "save" or similar words are used in the context of the present invention, they are to be understood as including reference to the retaining or holding of data or information both permanently and/or temporarily in the storage means, device or medium for later retrieval, and momentarily or instantaneously, for example as part of a processing operation being performed.

Additionally, where the terms "system", "device", and "machine" are used in the context of the present invention, they are to be understood as including reference to any group of functionally related or interacting, interrelated, interdependent or associated components or elements that may be located in proximity to, separate from, integrated with, or discrete from, each other.

Furthermore, in embodiments of the invention, the word "determining" is understood to include receiving or accessing the relevant data or information.

In the embodiment of the invention, the display 22 for displaying the user interface 24 and the user input means 26 are integrated in a touchscreen 42. In alternative embodiments these components may be provided as discrete elements or items.

The touchscreen 42 is operable to sense or detect the presence and location of a touch within a display area of the device 12. Sensed "touchings" of the touchscreen 42 are inputted to the device 12 as commands or instructions and communicated to the controller 18. It should be appreciated that the user input means 26 is not limited to comprising a touchscreen, and in alternative embodiments of the invention any appropriate device, system or machine for receiving input, commands or instructions and providing for controlled interaction may be used, including, for example, a keypad or keyboard, a pointing device, or composite device, and systems comprising voice activation, voice and/or thought control, and/or holographic/projected imaging.

Input may also be received via at least one sensor which is part of a sensor system or a set of sensors 44 of the device 12. Individual sensors within the set of sensors 44 are operable to monitor, sense and capture or otherwise gather or measure sensor data and/or information associated with or relating to one or more characteristics, properties and parameters of the device 12, the surrounding environment, or components, systems or devices associated therewith or coupled thereto. For example, the set of sensors 44 is operable to sense and gather sensor data relating to a state of the device 12 and/or a state of the environment surrounding the device 12. In an embodiment, the state of the device 12 comprises a position of the device 12. In an embodiment, the state of the device 12 further comprises a velocity and/or speed of the device 12. The set of sensors 44 include an inertial sensor system comprising an acceleration sensor and an orientation sensor, a direction sensor and a position sensor. Alternative embodiments of the invention may comprise additional and/or alternative sensors, including a motion sensor, an infra-red sensor, a depth sensor, a three dimensional imaging sensor, an inertial sensor, a light source sensor, and a Micro-Electromechanical (MEMS) sensor.

The acceleration sensor is operable to measure an acceleration of the device 12 and produce an acceleration data. For example, the acceleration sensor may be an accelerometer. The orientation sensor is operable to measure a rate of change of the orientation (i.e., angular rate) of the device 12 and produce an orientation data. For example, the orientation sensor may be a gyroscope. The direction sensor is operable to determine a direction relative to the Earth's magnetic poles and produce a direction data. For example, the direction sensor may be an electronic compass. The position sensor is operable to determine a position of the device 12 and produce a position data. For example, the position sensor may be a Global Positioning System (GPS). The use and operation of such sensors is well-known to persons skilled in the art and need not be described in any further detail herein except as is relevant to the present invention.

The at least one representation, which may be a first representation, may comprise one or more visual representations of the body 14. In the embodiment described, the first representation comprises a set of visual representations of the body 14. Accordingly, the set of sensors 44 includes imaging means in the form of a digital camera operable to capture images or imagery comprising the visual representations. The camera is integrated with the device 12 in the embodiment. The imaging means may comprise any suitable system or device facilitating the acquisition of still and/or moving images. For example, in the case where the device 12 comprises an IPHONE® smartphone, the imaging means may be an iSight™ camera. The use and operation of cameras is well-known to persons skilled in the art and need not be described in any further detail herein except as is relevant to the present invention.

In this way, the device 12 is operable to capture an image(s)/imagery of any type or any human shape representations of the body 14 of the user 16.

In embodiments of the invention, the at least one representation may comprise a non-visual, and/or a non-visible representation of the body.

The controller 18 is operable, via execution of applications such as the analysing app (at step 201 of FIG. 2) to collect and process user inputs (at step 202 of FIG. 2), pertinent to the user 16 and the analysis being conducted. In the embodiment, the user inputs include demographic information and other participant characteristics and attributes, medical physiology and activity data. It further includes, but is not limited to, details such as gender, age, ethnicity, fitness, medical history and medical physiology (through, for instance, operable connection to a smart watch or other device to collect heart rate, blood pressure, haemoglobin, blood glucose and activity data). Although embodiments of the invention do not require all of these inputs, the additional information provided to the AI/ML process will improve the accuracy of the body composition and anthropometry estimates of the embodiment. Additionally, with more information, an individual will advantageously have elevated levels of accuracy when estimating their relative health and wellness risk, as well as their predictive health and wellness risk, in the embodiment.

The device 12 comprises operably connected/coupled components facilitating performance and operations as described, including appropriate computer chips (integrated circuits), transceiver/receiver antennas, and software for the sensory technology being used.

One or more sensors of the set of sensors 44 may be integrated with the device 12, as may be the case where it comprises an IPHONE® smartphone. Alternatively, the device 12 may be operably coupled to one or more of the above-described set of sensors 44.

A device database 46 or databank also resides on the storage 20 and is accessible by the controller 18 under control of the app. The controller 18 is arranged to interact with the device database 46 as appropriate to cause the device 12 to carry out actions including the respective steps, functions and/or procedures in accordance with the embodiment of the invention described herein.

Details stored or saved remotely, for example in one or more remote database modules residing on respective storage of one or more remote systems or devices 32, such as the BCT database 40 of the server 36, are accessible by the device 12 via the one or more communications link(s) 30. The controller 18 is arranged to facilitate user interaction with the one or more remote databases to make the remotely stored content available for use as required.

It will be understood that any of the database(s) described may reside on any suitable storage device, which may encompass solid state drives, hard disc drives, optical drives or magnetic tape drives. The database(s) described may reside on a single physical storage device or may be spread across multiple storage devices or modules.

The device database 46 is coupled to the controller 18 and in data communication therewith in order to enable information and data to be read to and from the device database 46 as is well known to persons skilled in the art. Any suitable database structure can be used, and there may be one or more than one database. In embodiments of the invention, the device database 46 can be provided locally as a component of the device 12 (such as in the storage 20) or remotely such as on a remote server, as can the electronic program instructions, and any other data or information to be gathered and/or presented.

Similarly, both of the RU and BCT databases 38 and 40 are coupled to the server 36 and are in data communication therewith in order to enable data to be read to and from the RU and BCT databases 38 and 40 as is well known to persons skilled in the art. Any suitable database structure can be used. Any one or both of the RU and BCT databases 38 and 40 can be provided locally as a component of the server 36 (such as in the memory device) or remotely such as on a remote server, as can the server set of software. In an embodiment, several computers can be set up in this way to have a network client-server application. In the embodiment described each of the RU and BCT databases 38 and 40 is stored internally in the memory device of the server 36 as partitions of a single database structure. In alternative embodiments of the invention, there may be more or less databases.

Particular components of the system 10 will now be described in further detail.

BCT Database 40

As will be described in further detail, the BCT database 40 comprises a unified large volume and diverse world database of human medical imaging, body composition, anthropometry, participant characteristics and attributes, medical physiology and epidemiological information which has been collected while simultaneously collecting human imagery of each participant. The BCT database 40 has rich human intrinsic and extrinsic body and health information.

The establishment of the BCT database 40 is a key component of the described embodiment of the invention. Unlike existing databases such as the world's largest and most recognized dataset, the National Health and Nutrition Examination Survey (NHANES) where some, but not all, of the aforementioned data types are collected at different times, in the embodiment of the invention, for each participant contributing details of their body to the BCT database 40, the multi-dimensional data types are collected at the same time and performed in parallel while also collecting human imagery to form the foundation of the unified BCT Database 40 (in embodiments of the invention, this may be done at different or over a period of times to gather additional data). This will now be described in further detail with reference to FIGS. 4 and 5 of the drawings.

In the embodiment, all human data collections are built upon systematic, ethical and empirically verified, internationally recognised standards and data quality control procedures. This seeks to ensure three important development requirements of the embodiment are achieved: i) high measurement fidelity between variables; ii) multi-level and secure data storage for a large volume and heterogeneous database; and iii) accurate and repeatable predictive ability.

The embodiment of the invention requires that details of the bodies of a large heterogeneous sample of contributing human participants representative of a global or world population is collected to enable CV, ML/AI approaches and models to be able to accurately estimate an individual's anthropometry and body composition. Participants contributing details of their respective body to the BCT database 40 are stratified for a wide variety of participant characteristics and attributes, including, for example, gender, age, ethnicity, fitness status, and health status. Ethnicities include, but are not limited to, Caucasian, Hispanic, Middle Eastern, Asian, Indian and African. Large samples of homogeneous cohorts within heterogeneous, global populations are required in the embodiment so participant-level variance and covariance between unified measurements can be correctly modeled. The scale of these unified data collections is unique to the embodiment of the invention advantageously presents a unified data collection protocol for the collection of 2D, 3D or 4D imagery while simultaneously collecting medical physiology, participant characteristics and attributes, anthropometry and body composition and epidemiology data from a world population.

This portion of the embodiment of the invention is particularly advantageous in the medical and health, fitness, insurance and government sectors as other technologies within the broader medical technologies field can only obtain accurate (102), assessable (101) and affordable (103) human body representation data when expensive 3D scanning technologies are used within calibrated laboratory environments. In this regard, the described embodiment of the invention is capable of achieving all three aspects of an ideal body composition estimation method as described hereinbefore with reference FIG. 1. In fact most of the prior art, if not all, failed to achieve an accuracy comparable to a medical body composition scan, which motivated the embodiment present invention.

In the embodiment of the invention, for each participant contributing to the BCT database 40, six general measurements of details of their respective body are performed in parallel, which forms the foundation of the BCT Database 40 (as depicted in FIG. 5 of the drawings). These details include:

i) participant characteristics and attributes (at step 501), including, for example, Gender, Age, Ethnicity, Fitness and Medical History;

ii) participant anthropometry (at step 502), including, for example, mass, height, waist, hips, chest, thigh, bicep, calf, and inseam, to name a few;

iii) a representation including 2D, 3D . . . nD imagery or other body representation data (at step 503), including, for example, one or more of photographs, video, depth images, 3D scans or 3D reconstructed point clouds or meshes;

iv) imagery capturing device intrinsic and extrinsic parameters (at step 506), including, for example, one or more of focal length, 3D pose and orientation (e.g. gyro data), resolution, size, and depth, field of view, rotation and translation with respect to a coordinate system. In the case of medical imaging such as DEXA/DXA scanners, these parameters can include additional data such as data to reference to a calibration pattern and phantom, the scanner pixel size referenced to an actual world measurement in, for example, cm or inches;

v) medical physiology measures (at step 507), including, for example, one or more of heart rate, systolic and diastolic blood pressure, VO2 max, blood samples for e.g. blood glucose and blood lactate levels, body temperature, ventilation and genomes;

vi) medical imaging data (at step 508), including, for example, one or more of PET, CT, MRI and DXA; and vii) epidemiology data (at step 509), including, for example, one or more of prediabetes, cardiovascular disease, joint osteoarthritis, mortality, falls incidence.

Measurement of the details recorded in the BCT database are referred to as being performed "in parallel" and "simultaneously". In the context of the embodiment of the invention, this generally refers to data being recorded within (preferably as short) a time period as is practicable for the data being collected so that natural human processes such as drinking, eating, dehydration or faecal matters, for example, do not affect the resulting measurements. For example, dehydration is reported to affect the accuracy of body composition scanners and generally speaking it is important to acquire the aforementioned body data within a short time to minimize or reduce any uncontrolled changes in body shape or weight, hence the term measuring data simultaneously and in parallel. Accordingly, these expressions are not to be limited to meaning at the same moment in real time, but within a time period as is practicable for the data being collected so that natural human processes such as drinking, eating, dehydration or faecal matters, for example, do not affect the resulting measurements.

In embodiments of the invention, additional data are collected at different time intervals to advantageously enable the creation and/or development of temporal modeling of participant (human) shape(s) and data gathered over time, and to derive statistically meaningful diagnostic trackers, and to achieve a physically meaningful risk analysis and/or trend.

In the embodiment, the BCT database 40 is a Health Insurance Portability and Accountability Act (HIPPA) compliant database, and all data is collected, processed and stored within the BCT database 40 in accordance with the ethical standards and procedures for research with human beings as per the relevant guidelines outlined by the World Health Organisation (WHO). All human data collected follows the ethical standards of the national, local, and institutional regulations and policies of the region(s) in which the human data is acquired, in the embodiment. From a technical perspective, this advantageously allows the technology of the embodiment of the invention to cluster and compare an individual versus global, local, based on one or more criteria from the human data (being) collected.

In the embodiment, details of the respective bodies of the participants contributing, including participant characteristic and attribute data such as, for example, gender, age, fitness, medical history and ethnicity are collected for the quality control of the data compiled within the BCT database 40. These are used for stratification and clustering of the data.

In the embodiment, as mentioned above, anthropometry data such as, for example, segment circumferences and segment lengths are recorded for each participant (at step 502). Each measurement is taken following the International Standards for Anthropometric Assessment (ISAK). In the embodiment, each measurement in this regard is taken twice. In the event that two measurements differ by more than 2% from each other, a third measurement is taken. The measure that is closest to the third measure is kept if it is within 2% of the third data point, and the other is discarded. In the embodiment, it is critical that this data is collected correctly as it is important for the training and development of accurate and repeatable CV/ML/AI models and techniques. This advantageously allows for the estimation of body circumference measures and generation of a 3D body shape and also for external validation by experts in the fields of these estimates. Accordingly, the embodiment of the invention advantageously incorporates anthropometry in addition to 2D/3D body shape, medical physiology and participant characteristic information for the training of ML/AI models. Furthermore, in additional tests, measurements of a qualified ISAK expert undergo statistical tests such as difference in means to identify any outliers or biases and assign a score factor representing confidence of certain measurements to a measurer. Such a process is also advantageous to identify strong reliable data necessary to train, validate and test ML prediction and regression models.

Advantageously in the embodiment of the invention, a representation in the form of human imagery of the respective body of each participant contributing details of their body is collected in parallel with the other key data of details collected for the BCT database 40, especially medical imagery. Although in the described embodiment, the process of capturing human 2D or 3D imagery data is implemented using a smart phone device (at step 503) as an affordable means, it is to be appreciated that all processes and protocols are also applicable to human 2D, 3D or 4D imagery or body representation data collected by a wide range of devices, including 3D scanners, stereoscopic, photographic or video devices, for example. These can include, but are not limited to, devices such as a) smart devices, b) a tablet, c) a PC or laptop, d) a web-camera, e) high and low resolution digital cameras, f) high and low resolution digital video recorders, g) high and low speed video (i.e., 50 Hz and 10,000 Hz), h) optoelectronic devices, i) infrared photography, j) thermal imaging and k) passive and active stereoscopic motion capture systems. By 3D, it is also meant any 3D shape representations as well as any time varying 2D representations. By 4D, it is also meant any time varying 3D representations.

In the embodiment, during the offline phase, and at the time 2D, 3D or 4D imaging is collected, each participant is prepared and guided as per a protocol devised to achieve highly reliable photography and video recording and follows a number of standards. This includes controlling for environmental factors such as lighting and background noise (e.g., object(s) that appear in the same volume as the participant). All participants are required to wear a standardised outfit. In the embodiment, this is form fitting in nature and made of material that does not alter scanners data, allowing for imagery or body representation data to accurately reflect an individual's body shape. It is important to note that these standards are important, in the embodiment, for accurate ground truth data, in the offline phase, but in the online phase individuals will be instructed to follow realistic and relaxed standards, invented novel CV, ML/AI approaches will then deal with varying background and other challenging issues arising during use of the system 10, to be described in further detail herein.

During the offline phase, the focal length, orientation (pitch, roll and yaw), image resolution, depth and height of the 2D, 3D . . . nD imagery device are also recorded. Indeed, generally all intrinsic parameters of the device are recorded in the embodiment. These are important measures for this embodiment as this data is required for the translation and rotation or generally projection, normalization and pre-processing of the human imagery (at step 503) and for registration and alignment with their corresponding medical imagery (at step 510) data. This is a further advantageous feature of the embodiment of the invention in which the BCT database 40 registers human imagery data with medical imagery data for the 2D and 3D segmentation of the human imagery data.

In the embodiment, variables such as medical physiology measures (at step 507) are also amongst the details measured in parallel to the human imagery, medical imagery and body composition data. Medical physiology data includes, but is not limited to, a) heart rate, b) systolic and diastolic blood pressure, c) $VO_2$ max, d) blood samples for e.g. blood glucose, Hb1 (Ac) and blood lactate levels, e) body temperature f) ventilation and g) genomes, of the respective body of the participant contributing to the BCT database 40. These parallel measures are again advantageous to the embodiment, the implementation using medical physiology data, with human imagery, anthropometry and epidemiological data in a unified module/system to predict an individual's body composition, prediabetes, chronic health and musculoskeletal disorder and mortality risk.

It is an advantage process, in the embodiment, that medical imaging data is collected and registered/aligned in parallel with human imagery and it is important, in the embodiment, that these two sets of data are registered to each other (for each respective participant body). From the medical imaging data (at step 508), both i) the imagery of an individual's full-body skeleton data/body shape (at step 510) and ii) body composition data (at step 511) are derived. It is important, in the embodiment, that medical imaging data contains both full body shape, skeletal and body composition data from a single calibrated medical imaging device. Uniquely and advantageously, this guides joint and anatomical landmark estimation, and segmentation procedures, which, as described in further detail hereafter, are used to estimate body composition from full body and segmented 2D images and 3D shapes of the individual.

In the embodiment, epidemiological data is obtained from each participant during data collections (cross-sectional), as well as prospectively at discrete time intervals following data collections (for example, 1 years, 2 years, 4 years, 8 years, 16 years etc.). Epidemiological data of the same participant repeated over time advantageously allows for the development of more accurate predictive health models and will further correct for errors presented in predictive equations currently used by health practitioners and researchers. Epidemiology data can be obtained from a variety of places, including, for example: 1) self-reported by the individual, 2) personal medical records of the individual, 3) government databases and so on, and 4) automatically detected data, for example, from a smart phone or via image and/or other processing. For self-reported data, in the embodiment, these will need to be verified by cross referencing with some type of medical record of the individual. In the embodiment, it is important that all epidemiological data is verified by a recognised medical entity to seek to ensure that all predictive ML models and equations for prediabetes, chronic health disease, musculoskeletal disorders and mortality are robust and met with high levels of specificity and sensitivity. Epidemiological data can include, but is not limited to, the diagnosis of prediabetes, diabetes, cardiovascular disease, cancer, incidence of mortality, a falls event, significant reduction in lean muscle tissue, joint osteoarthritis development, for example.

This is another advantageous feature of the embodiment of the invention. In this regard, much of the current prior art calculates body composition by fitting shapes and volumes to a 3D representation of an individual's body and linear regression methods with limited degrees of freedoms are then used to model the relationship between the volumes and shapes to body composition outputs calculated from MRI or CT scans. There is no attempt to register the anatomy of an individual obtained from the medical imagery (from step 510) onto a 2D or 3D representation of the individual, as in the embodiment. This highlights the limitations of previous approaches in their ability to reliably and repeatably segment the 2D and 3D shape of an individual as subject-specific anatomical information is not used to guide those approaches. Having anatomically (e.g. using the joints) guided data, shapes and body parts in the approach of the embodiment also allows for an accurate, fair and statistically meaningful comparison between one person to another or to track and compare the changes of a person over time.

BCT Database 40 Description of Quality Assurance and New Medical and Human Imagery Processing Techniques As will be described in further detail, quality assurance and pre-processing steps have been developed related to the capturing phase of medical images and medical data for the BCT Database 40 (FIG. 6*a*). Particularly, quality assurance and pre-processing techniques which have been developed for the BCT database 40 which are related to the capturing phase of human imagery which may be in the form of image or images, videos or video frames, 2.xD images including depth images and 3D body scans for the BCT database (FIG. 6*b*). Quality assurance and pre-processing steps have been developed which are related to the capturing phase of anthropometry data for the BCT database 40. Additionally, quality assurance and pre-processing steps which have been developed which are related to the capturing phase of dynamic data for the BCT database 40.

Prior to storage acceptance within the HIPAA compliant BCT database 40, the collected data undergoes a quality assurance protocol, specific to the embodiment of the invention, and image processing techniques for the human and medical imagery to identify anatomical landmarks and regions of interest, also specific to the embodiment of the invention. These data quality control procedures and image processing techniques are important, in the embodiment, for the correct registration of medical imagery data with human imagery data and for the development of reliable ML/AI models to predict body composition and the risk of chronic health and musculoskeletal disorders with high specificity and sensitivity.

Referring to FIG. 6 of the drawings, in accordance with the quality assurance protocol, all medical physiology, anthropometry and body composition details received is checked using a data confirmation algorithm prior to acceptance into the BCT database 40 (at step 601). Therein, prior to acceptance into the BCT database 40 each medical physiology, anthropometry and body composition variable (at step 602) is compared to a Gaussian distribution of the global-database of previously collected data (at step 603). A medical image confirmation algorithm (at step 604) then verifies the quality of the 2D and 3D medical imagery data (at step 605).

Through image processing techniques, anatomical landmarks are identified from the medical imagery, as depicted in FIG. 7 of the drawings. Initially, each of the medical images has been assessed visually by a trained researcher. During this visual inspection, specific anatomical landmarks from each medical image are digitised in either two dimensions (x,y Cartesian coordinates) or three dimensions (x,y,z Cartesian coordinates). This is dependent on whether the medical image was collected in 2D (e.g. DXA) or 3D (e.g. MRI or CT). The specific anatomical landmarks that are identified are the joint centres of upper and lower limbs (i.e., wrist, elbow, shoulder, hip, knee and ankle) (702) as well as the midpoint of the femoral neck. Additionally, a line or plane bisecting the top level of the iliac crest (i.e., pelvis) and inferior border of the mandible (i.e., chin), the level of the T12/L1 vertebrae and the inferior border of the phalanges of the feet are recorded (701).

Once a sufficiently large sample of medical images with visually defined 2D or 3D coordinates (702) and vectors/planes (701) had been collated, a ML/AI model was developed to semi-automate the procedures required to identify joint centre positions, vectors and planes defining an individual's anatomy from their medical imagery data. Referring to FIG. 8 of the drawings, in the embodiment, the input (801) variables for the ML/AI model are the participant characteristic data (804), experimentally measured anthropometric data (803) and the scaled 2D or 3D medical imagery (802). The output (806) of the ML/AI model is the scaled 2D or 3D medical imagery data with user defined 2D or 3D coordinates of the wrist, elbow, shoulder, hip, knee and ankle joints as well as the midpoint of the femoral neck (808). Outputs include vectors or planes bisecting the top level of the iliac crest, inferior border of the mandible, the level of the T12/L1 vertebrae and inferior boarder of the feet (807). These outputs are stored within the BCT Database 40.

Referring to FIG. 9 of the drawings, these participant specific anatomically relevant joint centres and planes are then used to segment or 'cut' the full body shape (901) into specific regions of interest. These regions of interest (ROI's), in the embodiment, include:
  i) Arms: a plane passing through the plane inferior to the chin, the shoulder joint centres, the plane superior to the pelvis and the plane inferior to the feet.
  ii) Legs: The proximal portion of the segment will be defined using a plane passing from the lateral border superior to the pelvis through the midpoint of the femoral neck. The distal portion of this segment will be the inferior border of the feet.
  iii) Head: the volume above the plane inferior to the chin.
  iv) Trunk: This region will be defined as the total body, minus the arms, legs and head (902).
  v) Android region: volume between the superior plane of the pelvis and a parallel plane 20% the vertical length (Y-axis) between the superior plane of the pelvis and the inferior plane of the mandible (i.e., chin) (903)
  vi) Gynoid region: volume between a plane positioned 1.5-times the vertical length (Y-axis) of the android region, placed inferior to the superior plane of the pelvis (Plane A) and a parallel plane placed inferior to Plane A, 2-times the length of the android region (904).
  vii) Visceral region: The visceral region is contained within the android region. The android region contains both visceral fat and subcutaneous fat with the subcutaneous fat forming an uneven layer around the abdominal cavity. The volume of this subcutaneous fat is calculated and then subtracted from the total android fat in the android region to give visceral fat. (905)

In the embodiment, it is important that these segments and regions are segmented reliably between participants, as these shapes in 2D and 3D are used with other input variables within a ML/AI model to predict an individual's segment and total body composition (i.e., total, segment and region lean mass and fat mass).

This anatomically guided approach used within the embodiment of the invention advantageously provides that every person's medical image in the BCT database 40 is mathematically defined with 2D or 3D coordinates (702), vectors and or planes (701) using participant specific anatomical information (i.e., joint centres and anatomical landmarks), not simplified geometric shapes. In order for a geometric human shape to be an ecologically valid representation of a human and its associated medical image obtained using a DEXA, CT or MRI scan, it must comply with anatomical definitions and be able to represent the accurate physical landmarks (e.g. joints) seen in the medical scan. In the embodiment, body composition characteristics and values do not only rely on the standard geometrical shape of a person (e.g. 3D shape scan) alone, but also require anatomical data such as valid joint centres.

The BCT database 40 of the embodiment is a unique data due to the rich and unique type of visual, medical and other clinical and physical statistical information data it has when compared against many existing database such as the National Health and Nutrition Examination Survey (NHANES), which is the worlds largest US database. In the embodiment, the BCT data are collected from various regions in the world and independently validated by experts in the fields.

CV, ML and AI Techniques and Models that Learn, Link Body Shape and Composition to Human Imagery The steps outlined and described above comprising:
  i) The collection of a large and heterogeneous database (i.e. the BCT database 40) where human imagery is collected in parallel with medical imagery and other data;
  ii) High levels of quality assurance for the data collected; and
  iii) The use of accurate anatomical joints and specified ROI's to define medical and human imagery;
were found to be important, in the embodiment, to provide i) sufficient; ii) accurate enough data inputs to allow the necessary CV/ML/AI algorithms to be trained to be able to repeatedly and accurately predict an individual's body composition and anthropometry; and iii) the use of accurate anatomical joints and quality assurance protocols allows for a robust and accurate unified representation of the data. Unified representations are an important process when using CV and ML in the embodiment of the invention. In simple terms, a unified representation is a way of representing data or imageries using a hierarchy structure that is unique and the same for all participants. As a very simple example, if the images needed for an ML model must be of size (M×N) and must be centered at the mid-hips position, then that means that any participant image of any image size will need to be normalized or pre-processed such that its size becomes (M×N) and the mid-hips position is placed at the centre.

The link or linking of the embodiment is an example of a relationship between body shape and composition and the human imagery. In other embodiments, additional and/or alternative relationships are possible. These may include being registered, and/or aligned, and/or matched to, a unified representation of the respective body of each participant.

In the embodiment, there are four processes (which may comprise of one or more different CV/ML/AI models), which have been developed off-line, that use machine intelligence learning of the relationships between the various components of the BCT database 40 and enable the estimation of body composition and body circumference from human imagery and the related participant characteristics and attributes, and medical physiology, of the details of the participants contributing to and stored in the BCT database 40.

Referring to FIG. 3 of the drawings, the first process comprises CV/ML/AI model developed offline (at step 301) is a model that can and is operable to estimate subject or user specific anatomical information and joints from a human image. The data within the BCT database 40 is used to train this model. Having both medical imagery containing joints and body composition as shown in FIGS. 14a-14d and human imagery collected simultaneously allows the CV/ML/AI models to be trained to estimate both joints and anatomical landmarks from just a human image.

Particularly, the images depicted in FIGS. 14a-14d show the original medical imagery (FIG. 14a) with joints highlighted in (FIG. 14b) for machine learning training. These joints allow the ML/AI algorithm to define the regions of interest shown in (FIG. 14c) and (FIG. 14d) shown against the skeleton and body composition image respectively regardless of the person pose (i.e. pose invariant).

Figures 15A, 15B:
FIGS. 15a and 15b depict how specific anatomically relevant landmarks and joint centres have been estimated based on a specific front and side human image using CV/ML/AI models trained using data in a BCT database 40 of the system of FIGS. 2 and 3.

The diagrams depicted in FIGS. 15a and 15b show how the specific anatomically relevant landmarks and joint centres have been estimated based on a specific front and side human image using CV/ML/AI models trained using data in the BCT database 40.

This estimation of joint centres and anatomical landmarks is an advantageous feature of this process of the embodiment of the invention, resulting in an improvement in the accuracy of the body composition and body measurement estimates. It should also be noted that the CV/ML/AI models developed can estimate a higher number of joint centres than just those shown in the diagram.

A second process (at step 302) has models developed to estimate body part segmentation using these anatomical landmarks based upon ROI's discussed previously and shown in FIG. 9. These ROI's and segments of the body are required, in the embodiment of the invention, and used by the system 10 to be able to estimate a variety of body composition estimates such as whole body and segment lean mass, total and central adiposity measures, as well as anthropometry such as body circumferences, areas, volumes and total body mass.

Figure 16:
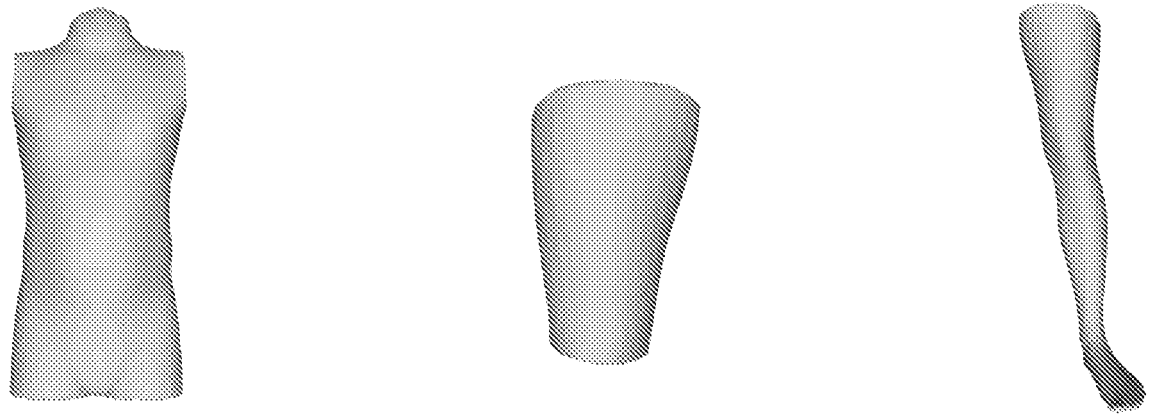
FIG. 16 depicts 3D segmentation without using anatomical landmarks and joint centres for body part segmentation.

This method of segmentation is advantageous to this process. Prior to the embodiment of the invention, segmentation of the body used to estimate body composition from 3D scanners was based on cutting the body into specific regions as shown in FIG. 16. The anatomical landmark and joint information was not determined and used as in the embodiment.

Figure 17:
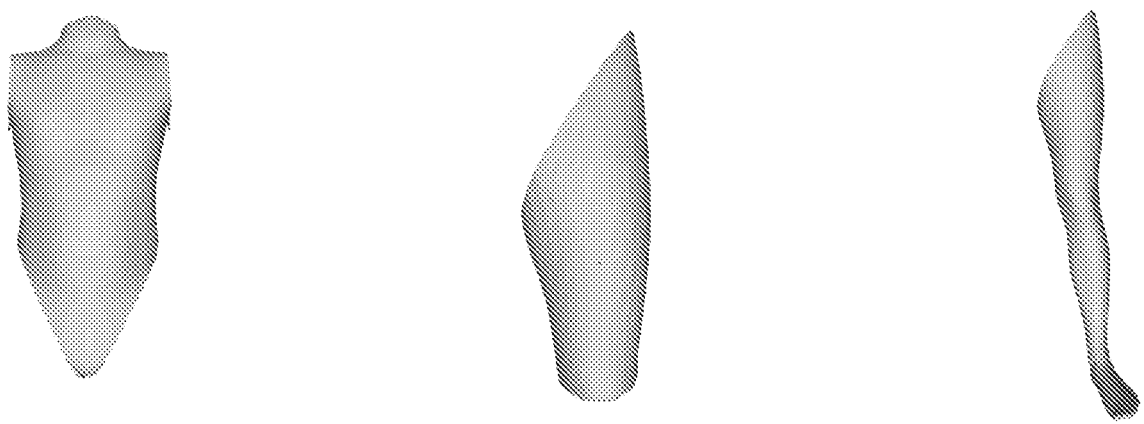
FIG. 17 depicts 3D segmentation using anatomical landmarks and joint centres for body part segmentation.

Via this advantageous method of segmentation, the system 10 is operable and able to estimate the anatomical landmarks and joints and as such is able to segment the body in a similar way to that used when segmenting medical imagery where actual joint information is available. The difference between the two methods can be seen by comparing the images in FIGS. 16 and 17, which show 3D segmentation without using (FIG. 16) and with using (FIG. 17) anatomical landmarks and joint centres for body part segmentation.

Figure 18:
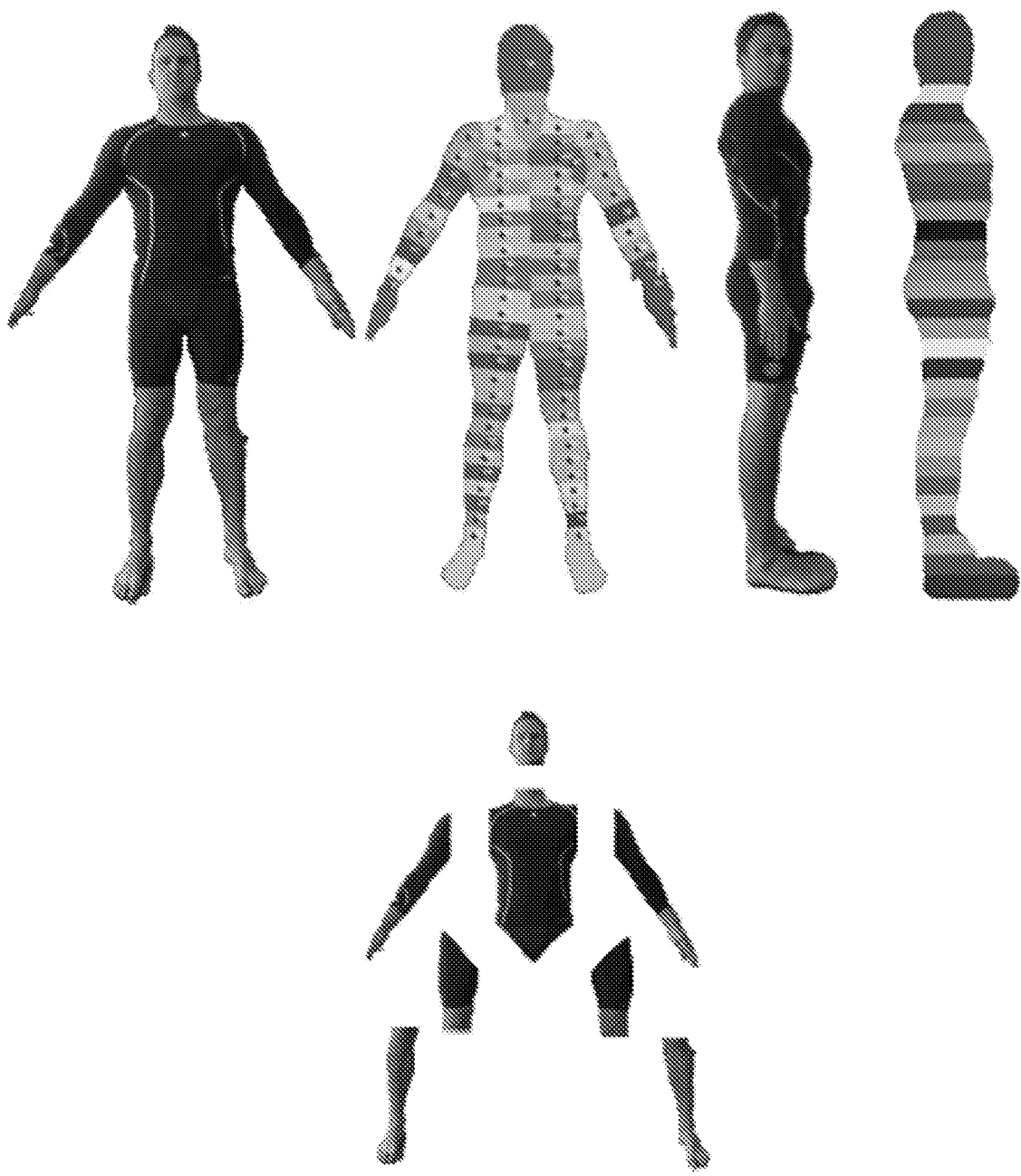
FIG. 18 depicts an example of how one type of 2D image features are prepared for a specific human image.

A third process (at step 303) involves processing of the data in the BCT database 40 to extract features and label image(s), 2D and 3D body shapes for the data in the BCT database 40 which is then used to train CV/ML/AI models. An example of how these features are prepared for a specific human image is shown in FIG. 18.

A fourth process (at step 304) involves the training of ML/AI models using the extracted features and label image (s), 2D and 3D body shapes for the data in the BCT database 40 combined with other medical physiology, participant characteristics and attributes to produce estimates of body composition and body measurements.

Preliminary results from a modeling approach for unseen participant data and using only 2D images of a participant using the system 10 of the embodiment were found to be as accurate as those results achieved using 3D scanners and linear regression based on latest published approaches in Ng et al. (Ng et al. (2016).Clinical anthropometrics and body composition from 3D whole-body surface scans.). The sample size of the inventors' preliminary results is also more than that used by state of the art, hence their approach is broader as it maintained the same accuracy but over a larger sample size and only using standard images.

As the size and diversity of the BCT database 40 increases, the processes and the image features extraction techniques of the system 10 lead to robust, improved, fine-tuned ML models with improvements in accuracy as the mutual relationship between different data is statistically meaningful and valid.

Device 12 with a Controller 18 to Control and Run Applications for Estimating Shape and Health Risk from Human Imagery Once the app is installed on the device 12, or the SDK or the service where the invention software is stored and running are called, the controller 18 is operable, under control of the analysing app, to present, via the touchscreen 42, a sequence of navigable electronic pages, screens and forms to the user 16 of the device 12 allowing for the inputting or capture of information and/or data, including data and/or information sensed via sensors of the set of sensors 44 such as images and imagery captured via the camera, instructions and commands pertinent to operation of the device 12 and the system 10.

In the embodiment described, the server software set of the server 36 comprises: a web server application, a registration and request application, an image processing application, a communication application, an invoicing/billing application, and a payment processing application.

As will be described in further detail, via the respective applications of the server software set, the server 36 is operable to perform functions and actions including: registration and sharing of user data; processing of data, including extracting, converting and combining data with data received via the app; and recording all real time data passing through the app interface.

The web server application is operable to deliver content relating to the system 10 via a dedicated website, such as web pages or other electronic pages or screens, to existing or potential users of the system 10. The website is accessible via a web browser of an Internet enabled mobile communication device, such as a notebook computer or a smartphone (including the device 12 in the embodiment), operably connected to be in data communication with the system 10 via a communication network. In the embodiment described, the means of data communication is through the Internet, however, other methods, such as direct connection, may be employed in other embodiments of the invention.

The content may include general information relevant to health and wellness, advertising and promotional or public relations information delivered via an appropriate one or combination of forums or medium including, for example, services provided under the trade marks YouTube™, Facebook™ and/or Twitter™.

The web pages that may be accessed include an online registration page 110, to be completed on first use of the system 10 by a user, and request pages 112. The website application is operable to enable a potential user of the system to manually register or record themselves as a user, thereby creating a personal account, and request an output from the system 10 to be displayed via the display 22 of the device 12. In the embodiment, the output comprises an estimation of the user's three-dimensional (3D) body shape and its associated body composition and health and wellness risks. The output may comprise an estimate of the user's: shape, physical, and ecological characteristics and/or at least one three dimensional (3D) shape and its associated anthropometry, body composition, and health and wellness risks. The body shape of the user outputted may be referred to as a second representation of the body, and may comprise an, or near, exact personalised subject specific image of the body of the user. The image provided may be referred to as an avatar. In this manner, a visualization of the analysis via at least one of text, images, meshes, 3D, videos, icons, virtual reality, and graphs, may be depicted in the output.

This is facilitated by the user completing and submitting to the server 36 (at steps 201 and 202), via the registration and request pages 110 and 112, communications in the form of electronic registration and request forms comprising user registration and request information, respectively.

The user registration information includes details comprising information and/or data relating to the user and their body including:

1) User Identification and Contact Details: Details facilitating identification and communication with the user. These details may comprise user's full private names, username for when using the system 10, private home address, physical and/or electronic mail address to be used for forwarding correspondence, contact telephone number, authentication information (such as a password), and any other unique and/or relevant identification information as applicable. This information is used by the system 10 for communicating with the user, including correspondence related to avatars created, using the system 10, and billing.

2) User Body Details: Information and/or data relating to the body of the user. In the embodiment described, this comprises anthropometric data of the body, including sex/gender, height, weight, clothes size (for example, small, medium, large, X-large, or XXL, to name a few), age/birthdate, and ethnic group. In alternative embodiments of the invention, additional and/or alternative details relating to and/or associated with the user's body may be requested.

3) Billing and Payment Details: Details facilitating billing and receiving payment from the debtor (person) responsible for paying for use of the system 10 by the user. The billing details may comprise a physical and/or electronic mail address to be used for forwarding correspondence including, for example, billing notices for processing and payment. The payment details may comprise details of a financial account, such as a credit card account of the debtor, stored and used to purchase items associated with actions performed via the system 10, such as the conducting of an analysis and the provision of an estimation in the embodiment. Additional and/or alternative payment processing platforms can be used, including, but not limited to PayPal and Bitcoin (BTC) services, for example, in embodiments of the invention.

The request information includes the first representation. As described previously, in the embodiment the first representation comprises a set of visual representations of the body 14. Preferably, visual representations within the set of visual representations comprise different views of the body 14, and they are captured (at steps 203-205) with the body 14 positioned in front of a contrasting, substantially clutter/noise free background. Particularly, in the embodiment described, the set of visual representations comprises, as a non-limiting example, two photographs of the body 14, being a first photograph of a front view of the body 14, and a second photograph of a side view of the body 14. To facilitate the capture and uploading of the two photographs, via the request page 112 the user 16 is able to access an image capture screen 114. The image capture screen allows for capturing and reviewing of the photographs before they are uploaded, and may comprise one or more sub-screens for guiding the user through the process. In the described embodiment, the device 12 is operable, via the controller 18 under control of an imaging app, to use data including orientation data produced via the internal gyroscope (of the orientation sensor calculating the orientation of the device 12) to ensure that the images are taken in the vertical plane for increased accuracy thereof.

The above process according comprises an image capture step to collect human imagery; videos, 2.xD or 3D images. At a minimum in the embodiment described this would comprise of a front and side photo, but, could also include other human imagery such as video or burst photography.

This could be an image capture step such as that described in the published specification for International Patent Application, Publication No. WO 2016/086266 in the name of MyFiziq Ltd, or the national phase patents/applications therefrom.

In alternative embodiments of the invention, the user registration and request information may comprise alternative or additional details, information and/or data.

All data and information collected via applications of the server software set, including the web server application and the registration application is distributed within the system 10 for use as described herein.

The RU database 38 has a plurality of RU records. Each RU record comprises a set of RU information relating to the account of an RU of the system 10, including the registration and request information as hereinbefore described, along with other information associated with the RU, such as outputs created therefor.

The server 36 has sensing means operable to sense or detect the receipt of communications comprising user registration and request information (sent via the dedicated website or other means as herein described). Upon sensing the receipt of such information, the server 36, via its processor under control of relevant applications of the server software set, including a database management module or application, is operable to generate, populate and manage records in the RU database 38, (as well as records in the BCT database 40) and to execute actions as described herein according to the data and information received.

A potential user can also register or record themselves as a user by providing the user registration information via email, facsimile, or other communication, which may be via a social networking service such as Facebook™ or Twitter™, for example, for automatic capture and entry into the RU database 38 by action of software of the set of server software or by a data entry operator or other employee of the administrator.

It should be noted that following successful registration, a RU may subsequently access the system 10 via an online access or "login" page, providing access to the system 10 once the user has entered an appropriate identification and security authorisation, such as their username and associated password.

The image processing application is operable to receive and process the submitted user body details and first representation of the body 16.

The processing comprises ML models responsible for an image inspection and processing step wherein human image(s) present in the one type of a first representation of the body are first inspected for the presence of a person and its body elements, within an optionally displayed guiding contour or image mask. Once the image(s) or the representation passes the inspection, another ML model trained to distinguish humans from other objects in image(s) then segments the human image only from the background scene (FIG. 18). In embodiments of the invention, this may comprise an initial image inspection and processing step such as that described in the published specification for International Patent Application, Publication No. WO 2016/086266 in the name of MyFiziq Ltd, or the national phase patents/applications therefrom, or an enhanced version of it as explained, depicted in FIG. 2.

The system 10 is then operable to implement a processing step to estimate joints from the human imagery (or videos, 2.xD or 3D images, if received). This step uses the ML/AI models developed offline and hereinbefore described (with reference to step 301) which have been built to estimate subject or user specific anatomical information and joints from human imagery (see also FIG. 15*a*, FIG. 15*b*).

The system 10 is then operable to implement a processing step to estimate body part segmentation from the human imagery and establish 2D and 3D regions of interest using the joints and anatomical landmarks in the previous step and the CV/ML/AI model developed offline and hereinbefore described (with reference to step 302).

The system 10 is then operable to implement a processing step to extract features and label image(s), 2D and 3D body shapes using the ML/AI model that has been developed and hereinbefore described (with reference to step 303).

The system 10 is then operable to implement a processing step where ML/AI model(s) uses the collected human images, features, labels and 2D and 3D body shapes calculated in the previous steps to estimate body composition and body measurements as hereinbefore described (with reference to step 304).

The system 10 is then operable to implement a step where estimated body composition and the body shape are output and displayed for the user via the display 22, together with a user trend, and future predictive body compositions based on their previous (if existing) and current estimates.

The communication application is operable to enable communication between the server 36 and devices in communication therewith. Such communication includes the communications described herein, and may be of any appropriate type including email, pop-up notifications, and SMS messages, and may be encrypted for increased security.

The user is able to navigate, including progressing to and returning from, the generated electronic screens and pages via execution of respective navigation interface element buttons provided thereon. Particularly, navigation bars 116 are provided having interface element buttons via which the user can control the system 10 to perform actions. In the described embodiment, such include: take a new image (have a new analysis conducted by the system/generate a new output estimation); and sign out/exit the system 10.

The invoicing/billing application is operable to generate an invoice for each registered user comprising an amount payable according to their usage of the system 10.

The payment processing application is operable to receive payment for each invoice.

In embodiments of the invention, one or more of the described, additional and/or alternative operations performed by the system 10 occur automatically, without requiring human intervention.

Health Risk Calculator Based on Estimated Body Composition and Anthropometry

The following outlines how the processed human imagery, related human features and estimated three-dimensional (3D) body shape, anthropometry and body composition data, together with the participant characteristics and medical physiology that have been input by the user can be used by the system 10 to allow the user to classify, assess and monitor their health and wellness risk.

In an offline phase, body fat classifications are developed using in-vivo percent body fat (PBF) cut-offs from the BCT database 40 and data from other public databases and visceral fat classifications are developed using in-vivo visceral fat (VF) cut-offs from the BCT database 40. Data and cut-offs are stratified for combinations of participant characteristic and attribute, medical physiology and epidemiology information (i.e., gender, age, ethnicity, health status, fitness, for example).

In an offline phase, predictive risk equations are developed using epidemiological data from peer reviewed prospective literature, including carrying out systematic reviews of literature to provide sufficient data, and epidemiolocal data from the BCT database 40 to develop prediabetic, diabetes, cardio vascular disease, musculoskeletal disorder, mortality and falls event risk equations.

An overview of a predictive risk equation is depicted in FIG. 10. The estimation of an individual's predictive health risk score (P-HRS) (1001), for example diabetes or cardio vascular disease, is a function of: their participant characteristics and attributes (PA), body shape (BS), medical physiology (MP) and body composition (BC) (1002). The specific dependent variables within each of these categories will have an associated Hazard Ratio (HR) (1003) at a predefined confidence interval (CI) (i.e., 90%, 95%, 99%, etc.) (1004). A HR is preferred as it not only considers the probability a health and wellness event will occur, but the timing of each event. If HR is not preferred by the user, risk ratios and odds ratios can also be utilised. The dependent variables (DV) (1005) and corresponding HR(CI) are dependent upon the health and wellness risk the individual is interested in assessing: therein, their risk of becoming prediabetic, developing a chronic disease or musculoskeletal disorder, premature mortality or incidence of a falls event (i.e., 1 years, 5 years, 10 years etc.). The HR(CI) for each DV are sourced from both the epidemiology data stored within the BCT database 40, as well as from the peer reviewed literature.

In an offline phase, a model was developed that uses machine intelligence learning of various statistical relationships between the various components of the BCT database 40 to allow the model to predict medical physiology and epidemiology from human imagery, the related participant characteristics and attributes, and estimated body composition and body circumference.

In an online phase the display 22 is used to show the user the following information:
i) Estimated body fat and estimated visceral fat are compared to the body fat classifications to display a general classification of body fat e.g. lean, normal, overweight and obese; and of visceral fat e.g. low risk, normal risk, elevated risk, high risk.
ii) Estimated body composition outputs and/or estimated circumference outputs are compared to the normative population distributions contained within the BCT database 40 for any combination of participant characteristic and attribute and medical physiology (i.e., gender, age, ethnicity, health status, fitness, for example), to show the user where they sit within a population distribution.
iii) An estimate of an individual's relative health risk score (RHRS) which is a function of their participant attributes, body shape, medical physiology and body composition. The specific variables used within each of these categories will depend on whether an individual is assessing their relative risk of prediabetes, chronic disease, musculoskeletal disorders, mortality incidence or falls risk. An individual's overall RHRS would be the low if their score placed them on the lower end of the health risk continuum and high if their score placed them on the upper end of the health risk continuum (for example, as depicted in FIG. 11).
iv) An estimate based on the predictive risk equations and/or ML/AI models calculated offline of the increased risk that the user is prediabetic.
v) An estimate based on the predictive risk equations and/or ML/AI models calculated offline of the increased risk of chronic health diseases.
vi) An estimate based on the predictive risk equations and/or ML/AI models calculated offline of the increased risk of musculoskeletal disorder, mortality and falls event risk.

vii) A step to detect sarcopenia either directed by the user or triggered by an estimated low muscle lean mass relative to height.

In an online phase, the system 10 is operable to allow the user to track changes in any estimated body composition or body measurement versus the most recent measurements and over time.

In an online phase, using the estimates calculated from the various predictive risk equations and body fat/visceral fat classifications the ability to identify 'at-risk' users allows early and tailored interventions to be recommended to the user over their lifespan to help improve a user's short and long term their health and wellness risk status.

The above and other features and advantages of the embodiment of the invention will now be further described with reference to the system 10 in use.

An interested person registers as a user of the System via the registration process as hereinbefore described, resulting in them being provided with a user account.

Thereafter, the (now registered) user accesses and uses the system 10 as hereinbefore described to conduct an analysis resulting in the generation of one or more outputs providing an estimation of their individual 3D body shape and its associated body composition and health and wellness risks.

Over time, the user may generate a sequence of such estimations, showing changes therein. Via such frequent self-monitoring the user is able to assess their progress towards a personal health and wellness goal and, accordingly, be more likely to achieve it.

It will be appreciated that the described embodiment of the invention provides several advantages as highlighted and described earlier herein.

In the context of seeking to provide an ideal body composition measurement tool, it can be seen that the described embodiment is affordable (103) and accessible (101) as the system 10 can be incorporated into a portable and easily available device such as a smartphone while also being accurate (102). It is the combination of the collection of the BCT database 40, the various quality assurance and medical imagery/human imagery processing techniques, and the development of advantageous CV, ML and AI techniques that enable the embodiment of the invention to be accurate while simultaneously being affordable and accessible.

The embodiment of the invention provides a database that has unlimited degrees of information of individuals as it has the actual 3D shape, images, videos and medical images and many other characteristics all collected simultaneously.

The approaches of the described embodiment are nearly fully automated and do consider the anatomical structure of the subject in addition to using higher order models including machine learning models to characterize or describe a subject with respect to their shape and other characteristics, unlike the prior art.

Another important advantage of embodiments of the invention is the registration and alignment of different data types and images captured by different sensors. Current sensing and imaging technologies, for example the work disclosed in International Patent Application Publication No. WO 2016/072926 A1, and the literatures surveyed in it, attempted to register or align an MRI-image(s) with another MRI-image(s) or medical images in general. In their work, both MRIs are acquired by the same MRI machine, of the same person, and in the same body pose, in a single scanning session. The same is valid when dealing with CT-scans. Unlike the present invention, their approach neither capture, nor utilise the person's actual coloured images/photos. In fact the methodology developed for the approach is not capable of aligning an MRI of a person to their coloured camera images even if these were available, also the person will have different poses and orientations in each image which will make it impossible for the approach to tackle the problem. Furthermore, MRI scanners and photo cameras use completely different sensors that require different models to physically represent the process of the sensing or capturing of the images. The work disclosed in WO 2016/072926 A1 was meant to provide an enhanced approach to clinicians dealing with a full body MRI scan (hence the word whole volume used in the specification of that application which does not mean an actual volume in litre or similar). Also, their approach was to provide better in labs MRI images to enable the calculation of body composition data such as bone structure and density, fat mass, lean mass water to name a few. The approach was also meant to provide a better visualization of accurately aligned MRI images so that they can track the same regions or certain image clusters accurately and make better assessments. The present invention is different and works differently from systems such as MRI systems. In the described embodiments, the present invention runs in a portable device such as a smart phone, the invented underlying approaches and algorithms are integrated and run in the device in a nearly fully automated way. They are based on novel and inventive approaches that are derived using (i) the subject characteristic data (e.g. height, weight, age, nationality etc.), (ii) MRI data including the body composition data, and (iii) the registration of the MRI images and the subject (person) images taken by the smart device camera or other camera. All of these different types of data, or features extracted from them, are combined, aligned and co-registered together to form a unique model of the subject and allow the AI and machine learning techniques to understand and learn differences between subjects and improve prediction when it compares a subject to the previously modeled subjects. Another critical difference between the present invention and the work described in WO 2016/072926 A1, is that they deform the bones during the alignment process. The described embodiments of the present invention do not alter bones during the alignment/registration as this is against the physics of deforming rigid elements such as a bone and will impact the ecological meaning of a human body.

In U.S. Pat. No. 8,588,495 B2, Gupta et. al. describes a system developed and claimed to do automatic diagnosis using medical images datasets. They used generative and discriminative learning to create a data atlas of the CT and MRI medical images, however, both are standard statistical analysis based upon methods employed by Gupta et. al. in 2010 which used mainly the image intensities to create the atlas. Similar to the work disclosed in WO 2016/072926 A1, Gupta et. al.'s work only deals with the registration of medical images against medical images. However, the described embodiments of the present invention deals with, registering, aligning and matching images of a person taken by a camera (e.g. a smart phone) and their medical images to create a unified representation. The complexity arises when dealing and co-registering images from two completely different sensors (e.g. MRI/PET and a camera). Also, the segmentation process in the described embodiments of the present invention deals with segmenting a person's image from noisy backgrounds and aligning the segmented images to the relevant medical image(s) of the person. In the hereinbefore described embodiments of the present invention, another type of segmentation is devised and implemented to segment the 3D body shapes into different parts. These processes are different from the segmentation process outlined in Gupta. et. al.'s invention where segments of the medical image are cropped utilizing existing software such as CAD from which diagnoses are classified. Importantly, in the described embodiments of the present invention, the risk analysis or diagnosing process is achieved via a portable smart device using only standard camera images that can be taken as frequently as needed, whereas the work of Gupta et. al. requires an actual MRI scan to do the automatic diagnose, which is costly and cannot be acquired regularly due to the risk of repeated radiation exposure.

It will be appreciated by those skilled in the art that variations and modifications to the invention described herein will be apparent without departing from the spirit and scope thereof. The variations and modifications as would be apparent to persons skilled in the art are deemed to fall within the broad scope and ambit of the invention as herein set forth.

The invention claimed is:

1. A portable device for analysing a subject body or a part thereof, the device comprising:
    a controller;
    storage storing electronic program instructions for operating the controller; and
    an input means, the input means comprising at least one sensor operable to capture at least one representation of the subject body or the part thereof, the at least one sensor comprising at least a camera and the at least one representation of the subject body or the part thereof comprising a visual representation captured by the camera;
    wherein the controller is operable, alone and/or in cooperation with one or more remote devices, and guided by the instructions of the electronic program, to:
        receive input via the input means, the input comprising the at least one representation of the subject body or the part thereof;
        process the input to conduct an analysis of the subject body or the part thereof and generate an output on the basis of the analysis, the processing comprising using at least one of a machine learning (ML) and/or artificial intelligence (AI) algorithm to estimate body composition, anthropometric variables and/or medical physiology, wherein the machine learning (ML) and/or artificial intelligence (AI) algorithm is trained using an ecologically and physically valid unified representation(s) of a human body and its anatomical structure,
        the unified representation(s) of a human body and its anatomical structure being a model or analogy of the human body, and being created from a dataset of contributed details, said dataset being processed, prepared, and quality assured using anatomical landmarks of the human body estimated using at least one computer vision (CV), machine learning (ML), and/or artificial intelligence (AI) technique,
        the contributed details comprising a visual representation of at least one human body contributing details to the dataset, and other respective data and/or information, including at least one medical image, of the at least one human body contributing details to the dataset,
        the other respective data and/or information being registered, aligned, segmented, and matched to the visual representation of at least one human body contributing details to the dataset using anatomical landmarks of the human body estimated using the at least one CV, ML, and/or AI technique to create the unified representation(s) of the human body and its anatomical structure; and
        communicate the output,
    wherein the output comprises the analysis of the subject body or the part thereof; and
    wherein said anatomical landmarks comprise a selected plurality of joint centres defining specific regions of interest (ROIs) in the subject body.

2. A device according to claim 1, wherein the at least one representation of the subject body or the part thereof comprises a visual representation comprising imagery, and/or a non-visual representation, meaning data that cannot be visualised.

3. A device according to claim 1, wherein the subject body or the part thereof being analysed belongs to a category and/or a group and/or a class, and the dataset comprises details of a plurality of different human bodies or the parts thereof belonging to the same, and/or a similar, category and/or group and/or class to that of the subject body or the part thereof being analysed, the details comprising data and/or information of, associated with, and/or related to each human body or the parts thereof of the plurality of different human bodies.

4. A device according to claim 3, wherein the data and/or information comprises, for each of a plurality of human participants contributing details of their respective bodies or the parts thereof to the dataset, one or more of human videos, photos, full and/or partial body shapes or surface scans, medical imaging, body composition, anthropometry, participant characteristics, participant attributes, medical physiology, and epidemiological information, which has been collected whilst collecting, and is linked, and/or registered, and/or aligned, and/or matched to, a respective visual representation to create an ecologically and physically valid unified representation of the respective body and its anatomical structure of each participant.

5. A device according to claim 4, wherein the collecting of the details occurs simultaneously and in parallel with collecting the respective visual representation.

6. A device according to claim 5, wherein additional data are collected at different time intervals to enable the development of temporal modelling of participant shape and data gathered over time, and to derive statistically meaningful diagnostic trackers, and to achieve a physically meaningful risk analysis.

7. A device according to claim 4, wherein the collecting of the details comprises capturing the details of each participant contributing to the dataset in accordance with quality assurance protocols and pre-processing processes and steps.

8. A device according to claim 7, wherein the at least one representation of the subject body or the part thereof comprises a visual representation comprising imagery, and/or a non-visual representation, meaning data that cannot be visualized, and wherein the processing comprises actions that include at least one of:
    analysing the collected data and/or information and the imagery using multi-dimensional statistical techniques and/or machine learning techniques and/or AI techniques and excluding imageries of the visual representation identified as outliers;
    classifying and clustering data and imageries into one or more of groups, regions, types, characteristics, and categories based on one or more labelling and/or annotation mechanism of the data type and/or an associated output linked to the data type;

estimating salient features and/or landmarks including anatomically relevant landmarks and/or key points and/or joint centres and/or bone links from any type of imagery of the body;

identifying and segmenting the body from cluttered backgrounds in imagery;

estimating body part segments from the imagery of the body constrained by anatomical features extracted from medical imaging and establishing regions of interest (ROI); and extracting image or generally shape features and labelled image(s) segments and/or image clusters and estimate their correspondence with the body data.

9. A device according to claim 1, comprising a display for displaying a user interface, wherein the controller is operable, under the guidance of the electronic program instructions, to communicate the output by displaying the output via the display depicting a visualization of the analysis via at least one of text, images, meshes, 3D, videos, icons, virtual reality, and graphs.

10. A device according to claim 1, wherein the subject body or the part thereof is that of an individual person, and the output comprises an estimate of the individual person's: shape, physical, and ecological characteristics and/or at least one three dimensional (3D) shape and its associated anthropometry, body composition, and health and wellness risks.

11. A device according to claim 1, wherein the at least one representation of the body is in the form of numbers and/or text and/or data and/or images of any type.

12. A device according to claim 1, wherein the anatomical landmarks comprise joint centres of upper and lower limbs, a midpoint of the femoral neck, a line or plane bisecting the top level of the iliac crest and inferior border of the mandible, a level of the T12/L1 vertebrae, and an inferior border of the phalanges of the feet.

13. A method for analysing a subject body or a part thereof, the method comprising:

storing electronic program instructions for controlling a controller of a portable device; and controlling the controller, alone and/or in cooperation with one or more remote devices, via the electronic program instructions, to:

receive input via input means of the portable device, the input means comprising at least one sensor operable to capture at least one representation of the subject body or the part thereof, the at least one sensor comprising at least a camera and the at least one representation of the subject body or the part thereof comprising a visual representation captured by the camera, the input comprising the at least one representation of the subject body or the part thereof; and process the input to conduct an analysis of the subject body or the part thereof and generate an output on the basis of the analysis, the processing comprising using at least one of a machine learning (ML) and/or artificial intelligence (AI) algorithm to estimate body composition, anthropometric variables and/or medical physiology, wherein the machine learning (ML) and/or artificial intelligence (AI) algorithm is trained using an ecologically and physically valid unified representation(s) of a human body and its anatomical structure, the unified representation(s) of a human body and its anatomical structure being a model or analogy of the human body, and being created from a dataset of contributed details, said dataset being processed, prepared, and quality assured using anatomical landmarks of the human body estimated using at least one computer vision (CV), machine learning (ML), and/or artificial intelligence (AI) technique, the contributed details comprising a visual representation of at least one human body contributing details to the dataset, and other respective data and/or information, including at least one medical image, of the at least one human body contributing details to the dataset, the other respective data and/or information being registered, aligned, segmented, and matched to the visual representation of at least one human body contributing details to the dataset using anatomical landmarks of the human body estimated using the at least one CV, ML, and/or AI technique to create the unified representation(s) of the human body and its anatomical structure, and said anatomical landmarks comprising a selected plurality of joint centres defining specific regions of interest (ROIs) in the subject body.

14. A method according to claim 13, wherein the at least one representation of the subject body or the part thereof comprises a visual representation comprising imagery, and/or a non-visual representation, meaning data that cannot be visualised.

15. A method according to claim 13, wherein the subject body or the part thereof being analysed belongs to a category and/or a group and/or class and the dataset comprises details of a plurality of different human bodies or the parts thereof belonging to the same, and/or a similar, category and/or group and/or class to that of the subject body or the part thereof being analysed, the details comprising data and/or information of, associated with, and/or related to each human body or the parts thereof of the plurality of different human bodies.

16. A method according to claim 15, wherein the data and/or information comprises, for each of a plurality of human participants contributing details of their respective bodies or the parts thereof to the dataset, one or more of human videos, photos, full and/or partial body shapes or surface scans, medical imaging, body composition, anthropometry, participant characteristics, participant attributes, medical physiology, and epidemiological information, which has been collected whilst collecting, and is linked, and/or registered, and/or aligned, and/or matched to, a respective visual representation to create an ecologically and physically valid unified representation of the respective body and its anatomical structure of each participant.

17. A method according to claim 16, wherein the collecting of the details occurs simultaneously and in parallel with collecting the respective visual representation.

18. A device according to claim 17, wherein additional data are collected at different time intervals to enable the development of temporal modelling of participant shape and data gathered over time, and to derive statistically meaningful diagnostic trackers, and to achieve a physically meaningful risk analysis.

19. A method according to claim 16, wherein the collecting of the details comprises capturing the details of each participant contributing to the dataset in accordance with quality assurance protocols and pre-processing processes and steps.

20. A method according to claim 19, wherein the at least one representation of the subject body or the part thereof comprises a visual representation comprising imagery, and/ or a non-visual representation, meaning data that cannot be visualized, and wherein the processing comprises actions that include at least one of:
- analysing the collected data and/or information and the imagery using multi-dimensional statistical techniques and/or machine learning techniques and/or AI techniques and excluding imageries of the visual representation identified as outliers
- classifying and clustering data and imageries into one or more of groups, regions, types, characteristic and categories based on one or more labelling and/or annotation mechanism of the data type and/or an associated output linked to the data type;
- estimating salient features and/or landmarks including anatomically relevant landmarks and/or key points and/or joint centres and/or bone links from any type of imagery of the body;
- identifying and segmenting the body from cluttered backgrounds in imagery;
- estimating body part segments from the imagery of the body constrained by anatomical features extracted from medical imaging and establishing regions of interest (ROI); and
- extracting image or generally shape features and labelled image(s) segments and/or image clusters and estimate their correspondence with the body data.

21. A method according to claim 13, comprising controlling the controller, via the electronic program instructions, to communicate the output by displaying the output via a display depicting a visualization of the analysis via at least one of text, images, meshes, 3D, videos, icons, virtual reality, and graphs.

22. A method according to claim 13, wherein the subject body or the part thereof is that of an individual person, and the output comprises an estimate of the individual persons: shape, physical, and ecological characteristics and/or at least one three dimensional (3D) shape and its associated anthropometry, body composition, and health and wellness risks.

23. A method according to claim 13, wherein the anatomical landmarks comprise joint centres of upper and lower limbs, a midpoint of the femoral neck, a line or plane bisecting the top level of the iliac crest and inferior border of the mandible, a level of the T12/L1 vertebrae, and an inferior border of the phalanges of the feet.

24. A non-transitory, computer-readable storage medium on which is stored instructions that, when executed by a computing means, causes the computing means to:
- receive input via input means of a portable device, the input means comprising at least one sensor operable to capture at least one representation of a subject body or a part thereof, the at least one sensor comprising at least a camera and the at least one representation of the subject body or the part thereof comprising a visual representation captured by the camera, the input comprising the at least one representation of the subject body or the part thereof; and
- process the input to conduct an analysis of the subject body or the part thereof and generate an output on the basis of the analysis, the processing comprising using at least one of a machine learning (ML) and/or artificial intelligence (AI) algorithm to estimate body composition, anthropometric variables and/or medical physiology, wherein the machine learning (ML) and/or artificial intelligence (AI) algorithm is trained using an ecologically and physically valid unified representation(s) of a human body and its anatomical structure,
- the unified representation(s) of a human body and its anatomical structure being a model or analogy of the human body, and being created from a dataset of contributed details, said dataset being processed, prepared, and quality assured using anatomical landmarks of the human body estimated using at least one computer vision (CV), machine learning (ML), and/or artificial intelligence (AI) technique,
- the contributed details comprising a visual representation of at least one human body contributing details to the dataset, and other respective data and/or information, including at least one medical image, of the at least one human body contributing details to the dataset,
- the other respective data and/or information being registered, aligned, segmented, and matched to the visual representation of at least one human body contributing details to the dataset using anatomical landmarks of the human body estimated using the at least one CV, ML, and/or AI technique to create the unified representation(s) of the human body and its anatomical structure, and
- said anatomical landmarks comprising a selected plurality of joint centres defining specific regions of interest (ROIs) in the subject body.

25. A non-transitory, computer-readable storage medium according to claim 24, wherein the anatomical landmarks comprise joint centres of upper and lower limbs, a midpoint of the femoral neck, a line or plane bisecting the top level of the iliac crest and inferior border of the mandible, a level of the T12/L1 vertebrae, and an inferior border of the phalanges of the feet.

* * * * *

UNITED STATES PATENT AND TRADEMARK OFFICE
CERTIFICATE OF CORRECTION

| | | |
|---|---|---|
| PATENT NO. | : 12,201,415 B2 | Page 1 of 1 |
| APPLICATION NO. | : 17/417163 | |
| DATED | : January 21, 2025 | |
| INVENTOR(S) | : Vlado Bosanac et al. | |

It is certified that error appears in the above-identified patent and that said Letters Patent is hereby corrected as shown below:

On the Title Page

At item (57), Line 13, "individuals" should be -- individual's --.

In the Claims

At Column 46, Line 54, "device" should be -- method --.

At Column 47, Line 8, "outliers" should be -- outliers; --.

Signed and Sealed this
Third Day of June, 2025

Coke Morgan Stewart
*Acting Director of the United States Patent and Trademark Office*